(12) United States Patent
Kajiwara

(10) Patent No.: US 12,376,753 B2
(45) Date of Patent: Aug. 5, 2025

(54) BIOLOGICAL DATA OBTAINING DEVICE, BIOLOGICAL DATA OBTAINING SYSTEM, VEHICLE PROVIDED WITH BIOLOGICAL DATA OBTAINING DEVICE, AND METHOD OF OBTAINING BIOLOGICAL DATA

(71) Applicant: THE UNIVERSITY OF KITAKYUSHU, Fukuoka (JP)

(72) Inventor: Akihiro Kajiwara, Kitakyushu (JP)

(73) Assignee: THE UNIVERSITY OF KITAKYUSHU, Fukuoka (JP)

( * ) Notice: Subject to any disclaimer, the term of this patent is extended or adjusted under 35 U.S.C. 154(b) by 1007 days.

(21) Appl. No.: 17/466,549

(22) Filed: Sep. 3, 2021

(65) Prior Publication Data

US 2021/0393147 A1 Dec. 23, 2021

Related U.S. Application Data

(63) Continuation-in-part of application No. PCT/JP2020/008768, filed on Mar. 2, 2020.

(30) Foreign Application Priority Data

Mar. 8, 2019 (JP) ................................ 2019-042517

(51) Int. Cl.
*A61B 5/0245* (2006.01)
*A61B 5/024* (2006.01)
(Continued)

(52) U.S. Cl.
CPC ........ *A61B 5/0245* (2013.01); *A61B 5/02405* (2013.01); *A61B 5/0507* (2013.01); *G06K 7/10306* (2013.01); *H04B 17/318* (2015.01)

(58) Field of Classification Search
CPC . A61B 5/0245; A61B 5/02405; A61B 5/0507; A61B 5/0004; A61B 5/024;
(Continued)

(56) References Cited

U.S. PATENT DOCUMENTS

2014/0058254 A1 2/2014 Yamaji
2016/0100766 A1* 4/2016 Yoshioka ............. A61B 5/0082
600/301
(Continued)

FOREIGN PATENT DOCUMENTS

JP 2013-097670 A 5/2013
JP 2014-039666 A 3/2014
(Continued)

OTHER PUBLICATIONS

JP5848469B1_Description_20241022_1040.pdf—translation of JP5848469B1 (Year: 2016).*
(Continued)

*Primary Examiner* — Vladimir Magloire
*Assistant Examiner* — Yonghong Li
(74) *Attorney, Agent, or Firm* — Studebaker Brackett PLLC

(57) ABSTRACT

A biological data obtaining device includes a storage unit, a first generation unit, and a second generation unit. The storage unit is configured to store time-series data in which first to $N^{th}$ distance-based fluctuation data are arranged. The first to $N^{th}$ distance-based fluctuation data are obtained based on reflected waves which are reflected from a living body at different times, wherein $n^{th}$ distance-based fluctuation data indicates changes in signal strength with respect to distance. The first generation unit is configured to generate time-based fluctuation data by performing strength obtaining process. The strength obtaining process includes obtaining one corresponding strength information, wherein the one corresponding strength information is a signal strength based on reflected waves from a predetermined detection part of the living body. The second generation unit is configured to generate biological data of the detection part of the living body based on the time-based fluctuation data.

15 Claims, 24 Drawing Sheets

(51) Int. Cl.
  *A61B 5/0507*  (2021.01)
  *G06K 7/10*  (2006.01)
  *H04B 17/318*  (2015.01)

(58) Field of Classification Search
  CPC ....... A61B 5/05; A61B 5/0816; A61B 5/1102;
    A61B 5/113; A61B 5/6893; A61B
    5/7207; A61B 5/725; A61B 5/7257; A61B
    5/726; A61B 5/7264; A61B 5/6889;
    H04B 17/318; H04B 17/103; G06K
    7/10306
  See application file for complete search history.

(56) References Cited

U.S. PATENT DOCUMENTS

| | | | | |
|---|---|---|---|---|
| 2017/0360324 | A1* | 12/2017 | Mitani | A61B 5/7278 |
| 2018/0055437 | A1* | 3/2018 | Nakayama | A61B 5/74 |
| 2019/0029547 | A1* | 1/2019 | Watarai | A61B 5/6892 |
| 2019/0097865 | A1* | 3/2019 | Xu | A61B 5/113 |

FOREIGN PATENT DOCUMENTS

| | | | |
|---|---|---|---|
| JP | 5848469 B1 * | 1/2016 | |
| JP | 2017-167802 A | 9/2017 | |
| KR | 2018095340 A * | 8/2018 | ............... A61B 5/08 |

OTHER PUBLICATIONS

KR20180095340A_Description_20241022_1118.pdf—translation of KR20180095340A (Year: 2018).*
JP5848469B1_Fig2_translate.pdf (Year: 2016).*
JP5848469B1_Fig3A_translate.pdf (Year: 2016).*
KR20180095340A_Fig1_translate.pdf (Year: 2018).*
KR20180095340A_Fig10_translate.pdf (Year: 2018).*
Masakazu Tsutsumi, "Contactless sleep monitoring for health management", Iryou kikigaku, Aug. 1, 2013, vol. 83, No. 4, pp. 371-373.
International Search Report issued in PCT/JP2020/008768; mailed Jun. 2, 2020.
International Preliminary Report on Patentability and Written Opinion issued in PCT/JP2020/008768; mailed Sep. 23, 2021.

* cited by examiner

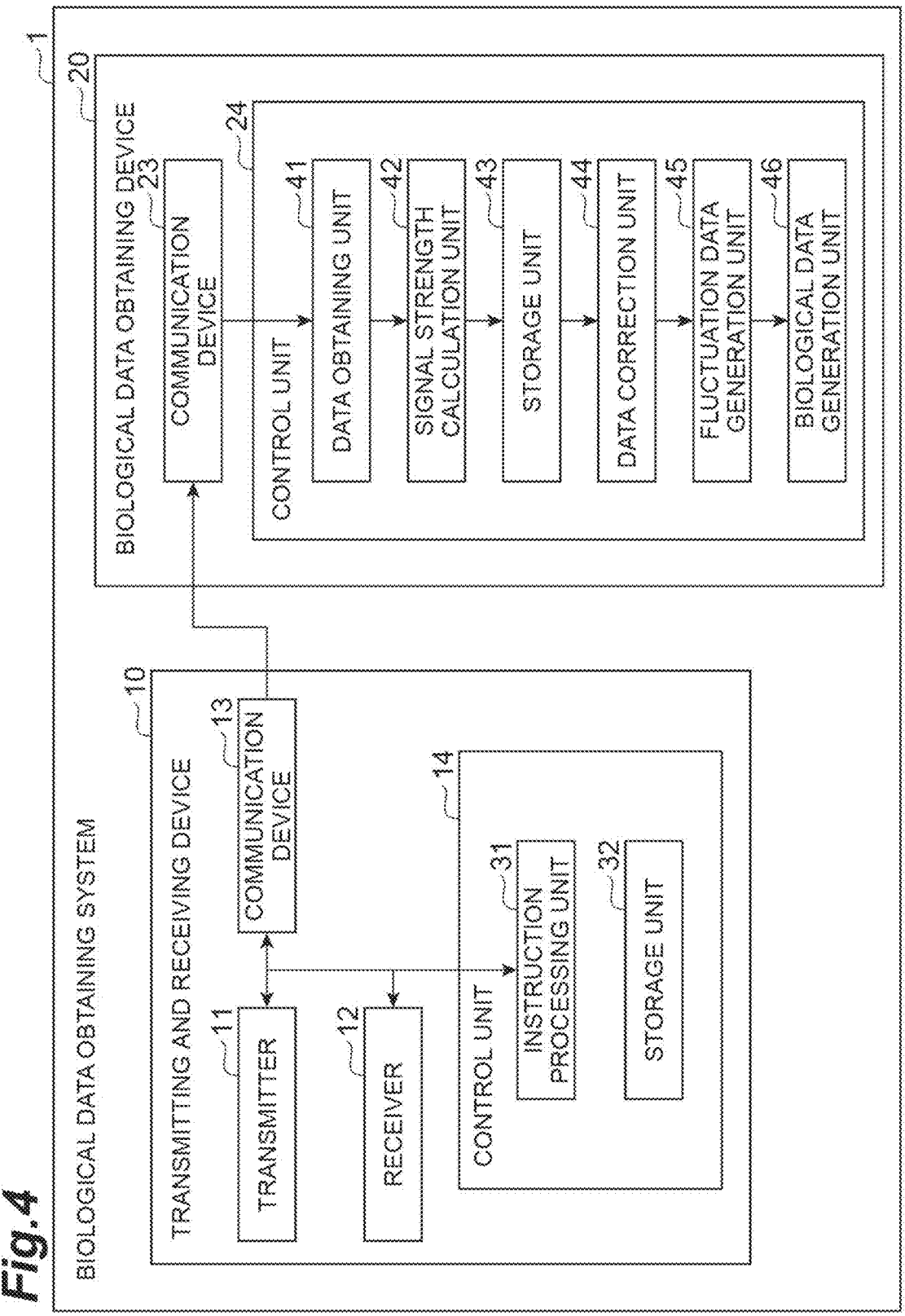

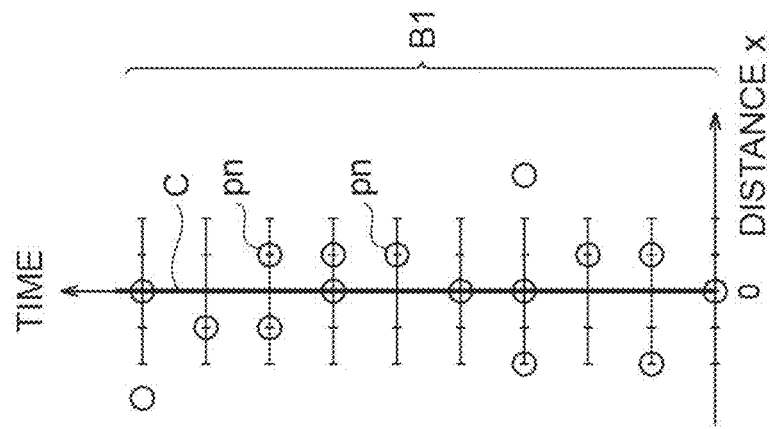
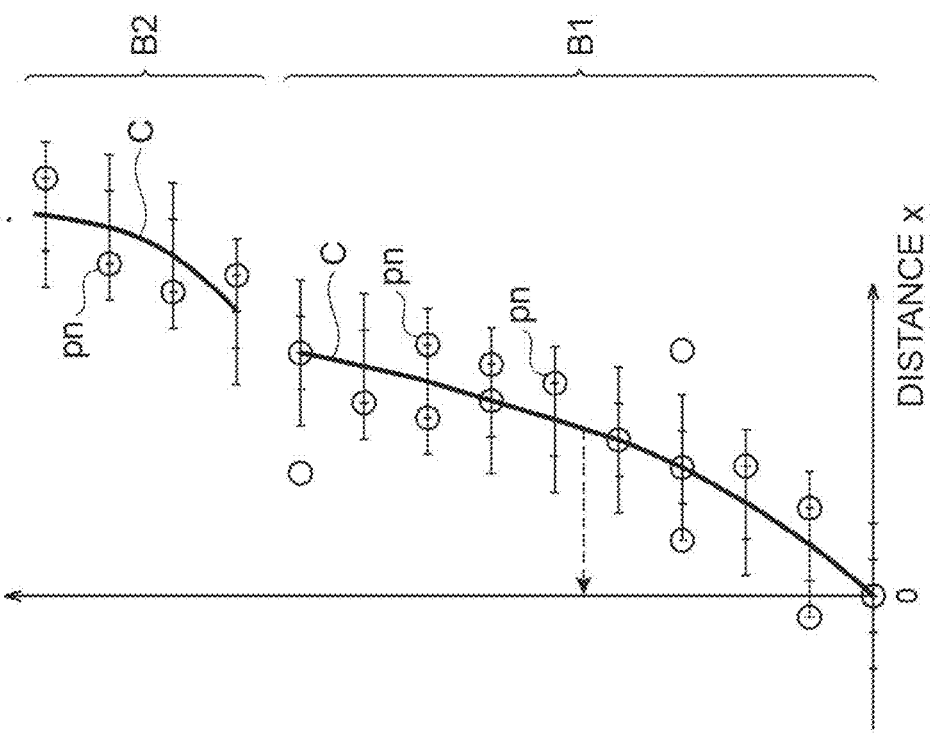

BIOLOGICAL DATA OBTAINING DEVICE, BIOLOGICAL DATA OBTAINING SYSTEM, VEHICLE PROVIDED WITH BIOLOGICAL DATA OBTAINING DEVICE, AND METHOD OF OBTAINING BIOLOGICAL DATA

CROSS-REFERENCE TO RELATED APPLICATION

This application is a continuation-in-part application of PCT Application No. PCT/JP2020/008768, filed on Mar. 2, 2020, which claims the benefit of priority from Japanese Patent Application No. 2019-042517, filed on Mar. 8, 2019, the entire contents of which are incorporated herein by reference.

BACKGROUND

Field

The present disclosure relates to a biological data obtaining device, a biological data Obtaining system, a vehicle including a biological data obtaining device, and method of obtaining biological data.

Description of the Related Art

Japanese Unexamined Patent Publication No. 2017-167802 discloses a wearable device that measures heartbeat data relating to the user's heartbeat. The wearable device transmits the user's heartbeat data and identification information to a transmission target terminal. This wearable device is a wristband type or wristwatch type measurement device, and the heartbeat data of the user wearing the wearable device are measured.

SUMMARY

An example biological data obtaining device includes A biological data obtaining device includes a storage unit, a first generation unit, and a second generation unit. The storage unit is configured to store time-series data in which first to $N^{th}$ distance-based fluctuation data are arranged in time series order. The first to $N^{th}$ distance-based fluctuation data are obtained based on reflected waves which are reflected from a living body at different times arranged in time series order, wherein the reflected waves are wide band radio waves or ultra wide band radio waves, wherein $n^{th}$ distance-based fluctuation data of the first to $N^{th}$ distance-based fluctuation data indicates changes in signal strength with respect to distance. N is a natural number of 2 or more, and n is a natural number of 1 to N. The first generation unit is configured to generate time-based fluctuation data in which a plurality of corresponding strength information are arranged in time series by performing strength obtaining process on the first to $N^{th}$ distance-based fluctuation data. The strength obtaining process includes obtaining one corresponding strength information of the plurality of corresponding strength information, wherein the one corresponding strength information is a signal strength included in the $n^{th}$ distance-based fluctuation data and based on reflected waves from a predetermined detection part of the living body. The second generation unit is configured to generate biological data of the detection part of the living body based on the time-based fluctuation data.

BRIEF DESCRIPTION OF DRAWINGS

FIG. 4 is a block diagram schematically showing an example of a biological data obtaining system.

FIG. 6A and FIG. 6B are diagrams for describing a method of correcting time-series data.

DETAILED DESCRIPTION

Figure 1:
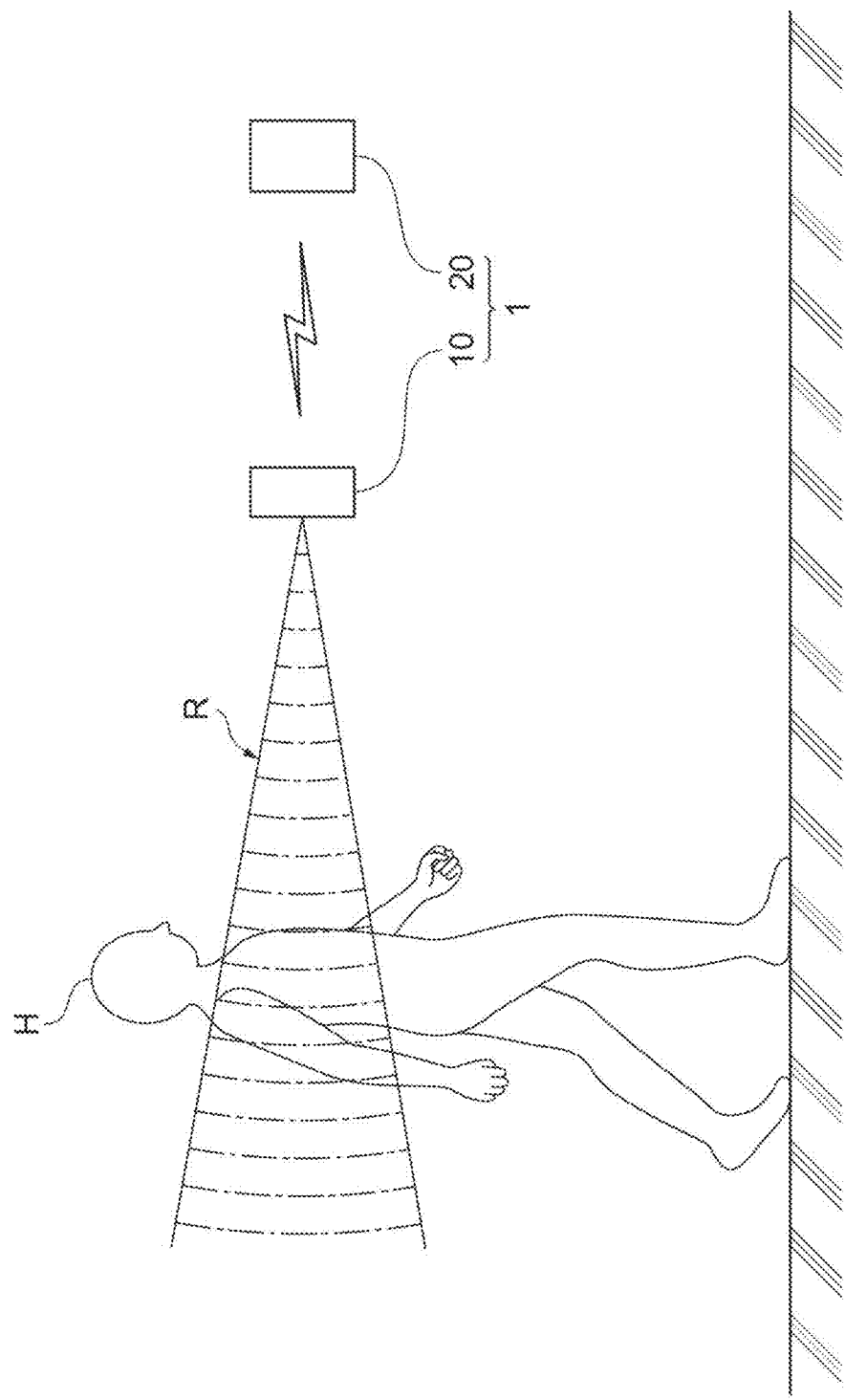
FIG. 1 is a schematic diagram schematically showing an example of a biological data obtaining system.
Figure 2:
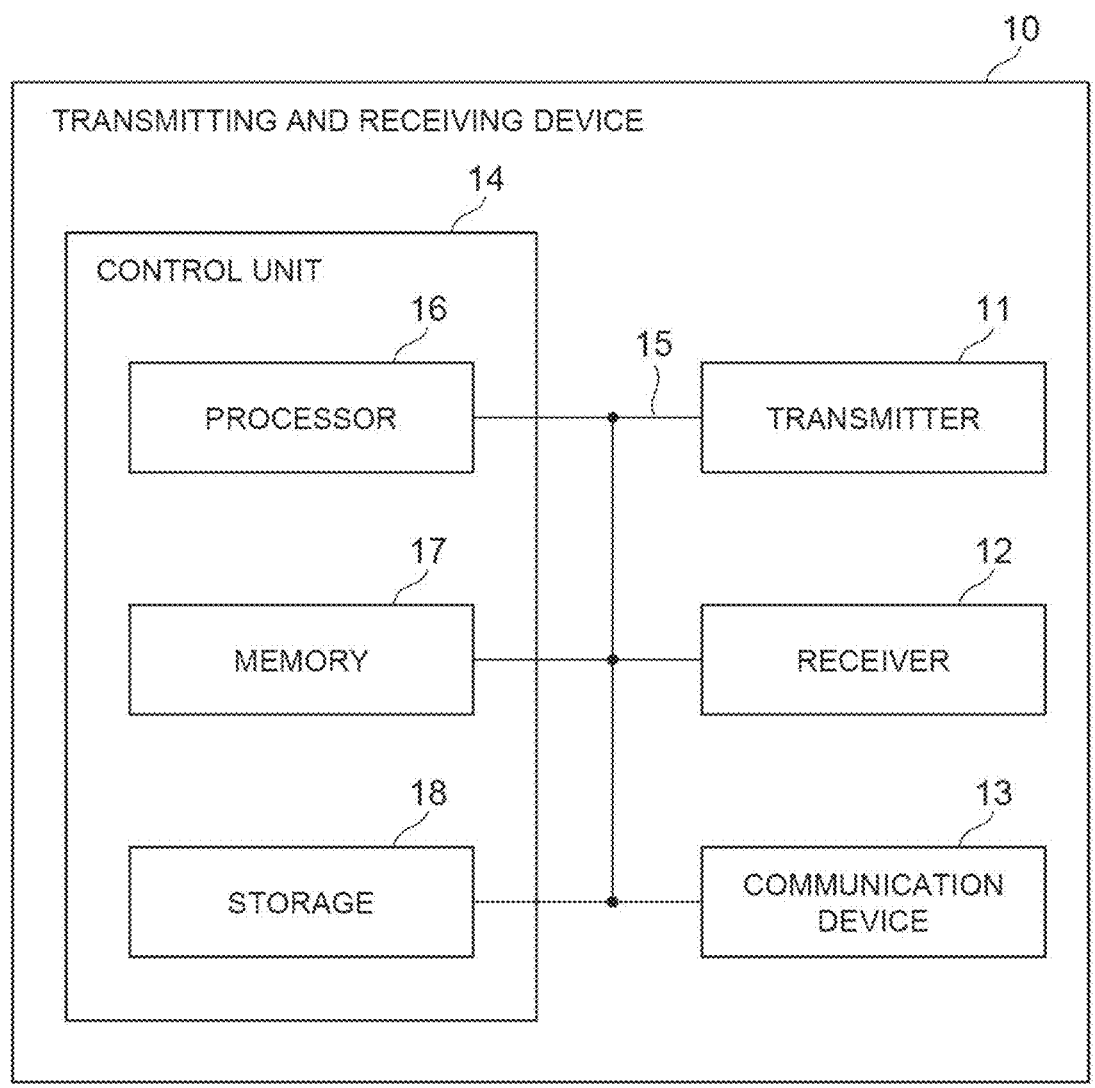
FIG. 2 is a block diagram schematically showing an example of a transmitting and receiving device.

In the following description, with reference to the drawings, the same reference numbers are assigned to the same components or to similar components having the same function, and overlapping description is omitted, Biological Data Obtaining System The configuration of a biological data obtaining system 1 will be described with reference to FIGS. 1 to 3. The biological data Obtaining system 1 includes a transmitting and receiving device 10 and a biological data obtaining device 20. The biological data obtaining system 1 may be configured to obtain biological data, such as respiration or pulsation, at a detection part of a living body H which is indoors or outdoors. Examples of indoors include the inside of a living room, an office, a bedroom, a toilet, a bathroom, a vehicle, and the like.

Examples of the living body H as a detection target include humans and animals. In this specification, explanation will be given with a human being as the living body H. The living body H may move, may work while sitting on a chair or the like, or may be stationary. Even if the living body H is stationary, a body of the living body H may move slightly unconsciously. In this specification, the "movement" of the living body H includes intentional movements by the living body H, slight movements (micro-movements) made unconsciously, and movements (vibrations and the like) that occur in the living body H due to external factors. The intentional movement by the living body includes the movement of the whole living body and the movement of a part of the living body. The movement of the whole living body includes, for example, walking or the like. The movement of a part of the living body includes, for example, the movement of a part of the living body in a standing position, a sitting position, and a lying position. The detection part may be, for example, a part (chest or back) including a heart portion of the living body H.

The transmitting and receiving device 10 is configured to transmit wide band radio waves or ultra wide band (UWB) radio waves toward a detection region R set in advance as a target region for detecting biological data. For example, the detection region R is set so that the radio waves reach the detection part of the living body H. The transmitting and receiving device 10 may be provided on a wall in the room, for example. As shown in FIG. 2, the transmitting and receiving device 10 includes a transmitter 11 (transmitting unit), a receiver 12 (receiving unit), a communication device 13 (communication unit), a control unit 14, and a bus 15.

The transmitter 11 is configured to transmit the wide band radio waves or ultra wide band radio waves toward the detection region R based on the instruction by the control unit 14. The directivity angle of the transmitter 11 on the horizontal plane of the antenna may be, for example, about 40° to 80°, or may be about 60° to 80°. The directivity angle of the transmitter 11 on the vertical plane of the antenna may be, for example, about 30° to 40°, or may be 30° or less. The detection region R is set in accordance with the range of these directivity angles.

In this specification, it is assumed that the term "wide band" refers to a case where the frequency bandwidth is 100 MHz or more and 500 MHz or less. Therefore, the frequency bandwidths of the wide band radio waves transmitted by the transmitter 11 may be, for example, 100 MHz or more, or may be 300 MHz or more. The term "ultra wide band" is assumed to refer to a case where the frequency bandwidth exceeds 500 MHz. Therefore, the frequency bandwidths of the ultra wide band radio waves transmitted by the transmitter 11 may be, for example, 3 GHz or more, but may be 4 GHz or less considering the Radio Law and cost performance. When the wide band radio waves or the ultra wide radio waves are used, the power spectrum of the transmission output of the radio wave can be reduced, so that the influence of the radio wave on the living body H can be reduced. In the following, unless otherwise specified, "radio waves" means wide band radio waves or ultra wide band radio waves.

The receiver 12 is configured to be able to receive reflected waves of the radio waves transmitted from the transmitter 11. Since the transmitter 11 uses the radio waves that have wide band or ultra wide band, the receiver 12 may be configured to separate and receive the reflected waves of the radio waves in the time axis in accordance with the reflected path length. That is, the receiver 12 is configured to extract a signal for each of a plurality of range bins (determined by the frequency bandwidth) that are divided in a distance direction of the detection region R. The width of each of range bins may be, for example, 10 cm or less, or may be about 3 cm to 4 cm. The number of range bins in the detection region R can be appropriately changed in accordance with the width of the range bin and the size of the detection region R.

The time interval (sampling period) for data obtaining by the receiver 12 can be set as appropriate. In order to facilitate an extraction of pulsation components by the biological data obtaining device 20, the receiver 12 may oversample the reflected waves based on a reference frequency corresponding to the pulsation of the living body. The extraction of pulsation components will be described in detail later. The receiver 12 may oversample the reflected wave at a sampling frequency that is greater than twice an upper limit value (for example, 1.6 Hz) of the frequency range in accordance with the pulsation. For example, the sampling frequency may be an integral multiple of the upper limit value. An element other than the receiver 12 may perform oversampling.

The communication device 13 is configured to be able to communicate with a communication device 23 of the biological data obtaining device 20. The method of communication between the communication device 13 and the communication device 23 is not particularly limited, and may be, for example, wireless communication. Some examples of wireless communication include long term evolution (LTE), LTE-Advanced (ITE-A), SUPER3G, IMT-Advanced, 4G, 5G, Future Radio Access (FRA), W-CDMA (registered trademark), GSM (registered trademark), CDMA2000, Ultra Mobile Broadband (UMB), IEEE 802.11 (Wi-Fi), IEEE 802.16 (WiMAX), IEEE 802.20, UWB, Bluetooth (registered trademark), and other communication methods may be used.

The control unit 14 (controller) is configured to transmit and receive a signal to and from the transmitter 11, the receiver 12, and the communication device 13 through the bus 15 to control their operations. The control unit 14 may include circuitry. The control unit 14 includes, for example, a processor 16, a memory 17, and a storage 18.

When predetermined software (program) is loaded into hardware, such as the memory 17 and the storage 18, the processor 16 performs a predetermined calculation, and executes transmission of radio waves from the transmitter 11, reception of reflected waves received by the receiver 12, communication by the communication device 13, and reading or writing of data in the memory 17 and the storage 18. As a result, functions of the transmitting and receiving device 10 are realized.

The biological data obtaining device 20 is configured to obtain biological data of the living body H based on the reflected waves (reception data) received by the transmitting and receiving device 10. For example, when the living body H breathes, the chest expands and contracts accordingly. Therefore, the reception data includes information relating to the respiration of the living body H. In addition, the heart expands and contracts in accordance with the pulsation of the living body H. Therefore, the reception data also includes information relating to the pulsation of the living body H.

The biological data obtaining device 20 may Obtain at least one of the information relating to respiration and the information regarding pulsation as biological data. As shown in FIG. 1, the biological data obtaining device 20 may be disposed apart from the transmitting and receiving device 10. The biological data obtaining device 20 may be provided, for example, in a place different from the room in which the living body H is present. A housing in which respective elements included in the biological data obtaining device 20 are housed may be separate from a housing in which respective elements included in the transmitting and receiving device 10 are housed.

Figure 3:
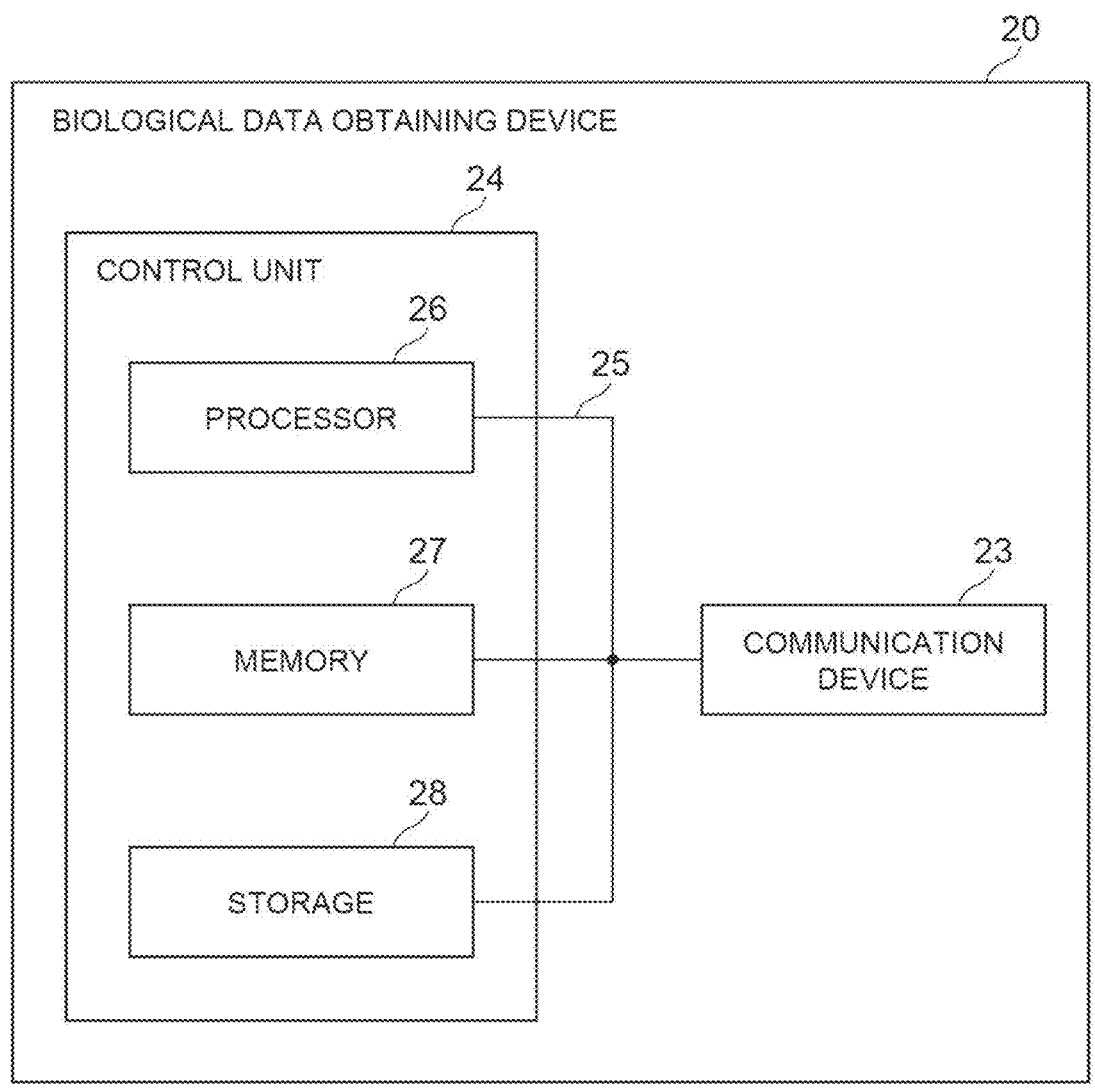
FIG. 3 is a block diagram schematically showing an example of a biological data obtaining device.

As shown in FIG. 3, the biological data obtaining device 20 includes the communication device 23, a control unit 24, and a bus 25. As described above, the communication device 23 is configured to be able to communicate with the communication device 13 of the transmitting and receiving device 10. The biological data obtaining device 20 may be formed of a computer device or a personal computer in which the communication device 23 is provided.

The control unit 24 is configured to transmit and receive a signal to and from the communication device 23 through the bus 25 to control operations of the communication device 23. The control unit 24 may include circuitry. The control unit 24 includes, for example, a processor 26, a memory 27 (storage unit), a storage 28 (storage unit).

When predetermined software (program) is loaded into hardware, such as the memory 27 and the storage 28, the processor 26 performs a predetermined calculation, and executes analysis of reflected waves obtained through the transmitting and receiving device 10, communication by the communication device 23, and reading or writing of data in the memory 27 and the storage 28. As a result, functions of the biological data Obtaining device 20 are realized.

Subsequently, each function of the transmitting and receiving device 10 and each function of the biological data obtaining device 20 will be described with reference to FIGS. 4 to 9. As shown in HG. 4, the control unit 14 of the transmitting and receiving device 10 includes a instruction processing unit 31 and a storage unit 32 as functional blocks.

The instruction processing unit 31 has a function of transmitting and receiving a signal to and from the transmitter 11, the receiver 12, and the communication device 13. For example, the instruction processing unit 31 transmits an instruction signal to the transmitter 11 so that the radio waves are transmitted from the transmitter 11. The instruction processing unit 31 receives data of the reflected waves (reception data in accordance with the reflected waves) from the receiver 12, and outputs the data to the communication device 23. The instruction processing unit 31 transmits an instruction signal to the communication device 13 so that the reception data are transmitted to the biological data obtaining device 20.

The storage unit 32 has a function of storing various kinds of data. Examples of the data stored in the storage unit 32 include program that has been read, operation setting data of the transmitter 11, and reception data relating to the reflected waves received by the receiver 12.

As shown in FIG. 4, the control unit 24 of the biological data obtaining device 20 includes a data obtaining unit 41, a signal strength calculation unit 42, a storage unit 43, a data correction unit 44 (correction unit), a fluctuation data generation unit 45 (first generation unit), and a biological data generation unit 46 (second generation unit) as functional blocks.

The data obtaining unit 41 has a function of obtaining reception data in accordance with the reflected waves through the communication device 13 and the communication device 23. The data Obtaining unit 41 outputs the obtained reception data to the signal strength calculation unit 42.

The signal strength calculation unit 42 has a function of calculating a signal strength in each of range bins based on the reception data output from the data obtaining unit 41. In other words, the signal strength calculation unit 42 calculates distance-based fluctuation data indicating changes in signal strength with respect to distance at a predetermined time. The distance-based fluctuation data indicates a signal strength in each of range bins. The signal strength calculation unit 42 may calculate the distance-based fluctuation data after performing difference process on the reception data by using reference reception data. The reception date may be obtained based on the reflection of the radio waves when the living body H is not present in the detection region R. This difference processing is performed, for example, to detect a person or a moving object, detect a distance of that or a movement line thereof, and reduce the influence of multipath.

Information including signal strengths calculated by the signal strength calculation unit 42 is output to the storage unit 43. Hereinafter, distance-based fluctuation data at time $t1, t2, \ldots, tN$ for each sampling period is referred to as "first distance-based fluctuation data", "second distance-based fluctuation data", ..., "$N^{th}$ distance-based fluctuation data" and the like. N is a natural number of 2 or more. Distance-based fluctuation data (one distance-based fluctuation data set) at time in of first to $N^{th}$ distance-based fluctuation data are referred to as "$n^{th}$ distance-based fluctuation data", wherein n is a natural number of 1 to N. The signal strength calculation unit 42 may calculate the first to $N^{th}$ distance-based fluctuation data at different times t1 to tN in time series order based on the radio waves reflected from the living body H.

The storage unit 43 has a function of storing various kinds of data. Examples of the data stored in the storage unit 43 include program that has been read, distance-based fluctuation data (a plurality of distance-based fluctuation data sets) calculated by the signal strength calculation unit 42, time-series data corrected by the data correction unit 44, time-based fluctuation data generated by the fluctuation data generation unit 45, biological data (for example, heartbeat interval data) generated by the biological data generation unit 46, and a set value indicating a storage unit of distance-based fluctuation data. Hereinafter, the time-series data that are corrected by the data correction unit 44 referred to as "corrected time-series data". The set value that indicates a storage unit of distance-based fluctuation data referred to as a "set time". The set time may be set in advance according to the capacity of the memory. The set time may be set within the range of, for example, about 20 seconds to 3 minutes, or may be 3 minutes or more.

Figure 5A:
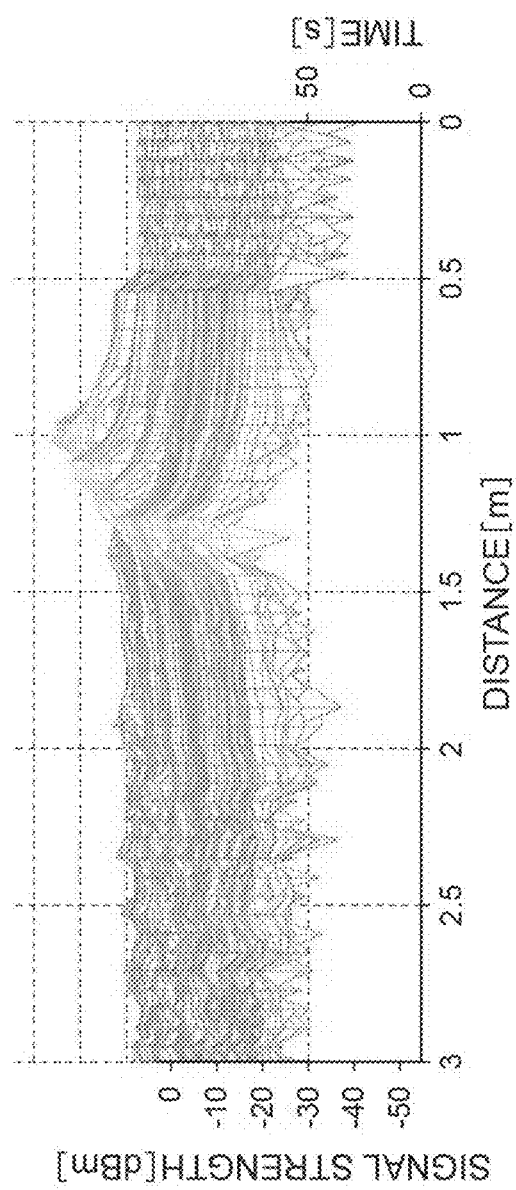
FIG. 5A is a diagram showing an example of time-series data.

The storage unit 43 stores time-series data in which the first to $N^{th}$ distance-based fluctuation data (first to $N^{th}$ distance-based fluctuation data within a predetermined time) are arranged in time series order. The first to $N^{th}$ distance-based fluctuation data are data calculated by the signal strength calculation unit 42 within the set time. The time-series data is illustrated by a three-dimensional graph including a distance (range) axis, a time axis, and a signal strength axis. The $n^{th}$ distance-based fluctuation data includes a distance component, a time component, and a signal strength component. FIG. 5A shows an example of time-series data. The time-series data shown in FIG. 5A are distance-based fluctuation data (a plurality of distance-based fluctuation data sets) obtained in 60 seconds. The time-series data is data obtained when, in a measurement environment in which a subject (living body H) faces the transmitting and receiving device 10, the measurement starts in a state in which the subject (living body H) is stationary at a location about 1.3 m away from the transmitting and receiving device 10 and gradually approaches the transmitting and receiving device 10 after about 30 seconds. In the time series data, signal strengths of the reflected waves from the chest and heart (detection part) of the subject appears near a peak of the distance-based fluctuation data, and distance components at the peak gradually decreases.

The data correction unit 44 has a function of correcting the time-series data stored in the storage unit 43. For example, the data correction unit 44 may perform correction process. The correction process includes correcting distance components of the $n^{th}$ distance-based fluctuation data so that a distance component corresponding to the detection part in the $n^{th}$ distance-based fluctuation data approaches a reference value. The reference value may be, fir example, a value arbitrarily set for one operation of obtaining biological data. The data correction unit 44 may set the position of the distance component at a peak of the first distance-based fluctuation data as the reference value. The data correction unit 44 may obtain corrected time-series data by performing the correction process on the first to $N^{th}$ distance-based fluctuation data. For example, the correction process may include a primary correction, a secondary correction and a tertiary correction. In the primary correction, the data correction unit 44 may approximate the movement of the living body H in one of a plurality of blocks that are obtained by dividing the first to $N^{th}$ distance-based fluctuation data. In secondary correction, the data correction unit 44 may correct a distance component corresponding to the detection part. In the tertiary correction, the data correction unit 44 may correct distance components between the plurality of blocks. The data correction unit 44 outputs the corrected time-series data to the fluctuation data generation unit 45.

Here, an example of correction process will be described. This correction process is performed in order to extract a signal (temporal change in signal strength) based on the reflection from the detection part even when the living body H was moving. First, the data correction unit 44 calculates peak (scattering point) in each of the first to $N^{th}$ distance-based fluctuation data. The "peak" calculated at this time may be a point at which the signal strength is larger than a predetermined value and is maximal value.

Due to influence of disturbance such as multipath, a plurality of peaks may be calculated for one piece of distance-based fluctuation data (one distance-based fluctuation data set). In this case, the time-series data may include peaks other than the peak based on the reflection from the detection part. FIG. 6A shows an example of a graph in which a plurality of peaks pn including peaks based on disturbance or the like are plotted with white circle marks on a plane of distance axis-time axis. Hereinafter, correction process for correcting the distance-based fluctuation data including peaks caused by disturbance or the like will be described using a plurality of peaks pn illustrated in FIG. 6A.

First, the data correction unit 44 performs a generation process. In the generation process, the data correction unit 44 draws an approximate line C based on a plurality of peaks pn for each of the plurality of blocks. The plurality of blocks are obtained by dividing the time-series data at predetermined time intervals (for example, intervals of several seconds to several tens of seconds) on the time axis. Hereinafter, the plurality of blocks obtained by sequentially dividing the time-series data in time series may be referred to as "first block B1", "second block B2", . . . , "$M^{th}$ block BM". M is a natural number of 2 or more. One block of the first to $M^{th}$ blocks B1 to BM may be referred to as "$m^{th}$ block Bm", m is a natural number of 1 to M.

The approximate line C means a movement trajectory that estimates a movement of the living body H within one block (within one predetermined time interval). The approximate line may be an approximate straight line or a polynomial approximate curve obtaining by using quadratic or polynomial approximation. The movement of a person is shown by an almost linear movement trajectory when the movement is within one second. Even when the movement is made in about several seconds, the movement trajectory can be approximated by a quadratic curve.

In the example of FIG. 6A, two scales are shown on each of the left and right sides of the approximate line C for each piece of distance-based fluctuation data. One scale interval corresponds to one range bin. That is, the scales in FIG. 6A are obtained by drawing two range bins on each of the positive side and negative side in the distance axis with the approximate line C as the center (with the approximate line C being put at the center). The data correction unit 44 may exclude peaks located outside the four range bins in subsequent processes. The number of range bins set in FIG. 6A is not particularly limited. For example, the number of range bins set may be one or k on each of the positive side and negative side in the distance axis with the approximate line C as the center, k is a natural number of 3 or more. The number of range bins set on the positive side in the distance axis with the approximate line C as the center may be the same as the number of range bins set on the negative side of the distance axis with the approximate line C as the center. The number of range bins set on the positive side in the distance axis with the approximate line C as the center may be smaller or larger than the number of range bins set on the negative side in the distance axis with the approximate line C as the center.

In general, a peak near the approximate C and the reflected waves from the vicinity of the chest match each other in many cases. However, when the living body H faces the transmitting and receiving device 10 in an oblique direction, a peak near the approximate line C and the reflected waves from the vicinity of the chest may be different. For this reason, the data correction unit 44 may detect a reflection point from the detection part in a predetermined range (hereinafter, referred to as a "scattering range") having the approximate line C as a reference line. For example, assuming that the living body H is a human being and its width in the horizontal direction is about 40 cm to 50 cm, when 1 GHz radio waves are used, the scattering range may be set to ±2 range bins from the approximate line C as shown in FIG. 6A. In this case, the width of the range bin may be about 15 cm.

Then, the data correction unit 44 performs the primary correction (block correction process) as shown in FIG. 6B. In the primary correction, the data correction unit 44 translates (performs parallel shift of) distance components of the distance-based fluctuation data included in the block B1 along the distance axis so that the approximate line C matches a reference value (for example, the position of x=0)

in the first block B1. The reference value in the block B1 is a value that is arbitrarily set. Then, the data correction unit 44 may calculate a temporal change in signal strength for each of range bins included in the scattering range and select a range bin in which the temporal change indicates a maximum value. For example, the data correction unit 44 may calculate a temporal change in signal strength for each range bin by calculating the difference in signal strength between $n^{th}$ distance-based fluctuation data and $(n+1)^{th}$ distance-based fluctuation data at the same range bins.

Figure 7B:
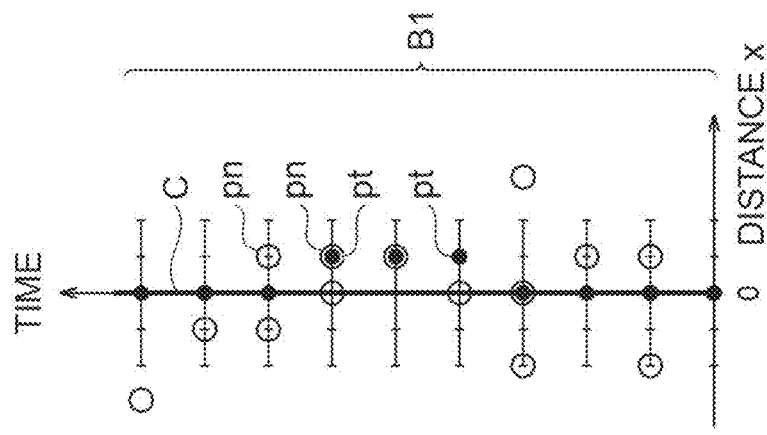
FIG. 7A and FIG. 7B are diagrams for describing a method of correcting time-series data.
Figure 7A:
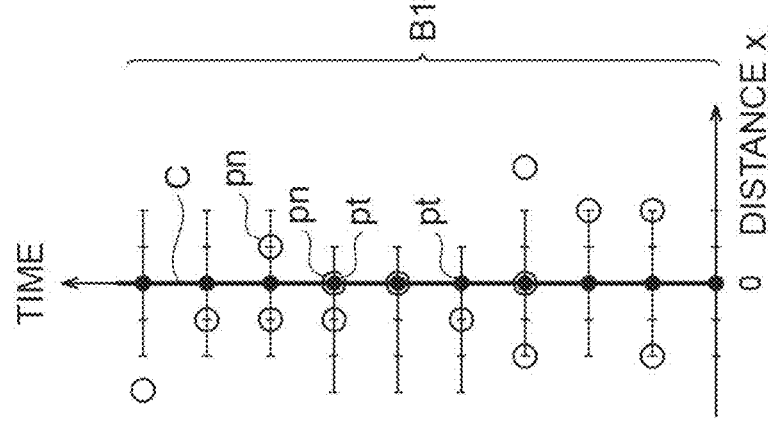

FIG. 7A shows an example of the result of detecting some points at each of which the temporal change in signal strength in the range bin is the largest. Some points detected in FIG. 7A are reflection points pt from the detection part. In FIG. 7A, the reflection point pt is indicated by a black circle mark. Then, the data correction unit 44 performs the secondary correction as shown in FIG. 7B. In the secondary correction, the data correction unit 44 translates (performs parallel shift of) distance components of the distance-based fluctuation data included in the block B1 along the distance axis so that distance components of the detected reflection points pt match a reference value. Some points at each of which the temporal change in signal strength in the range bin is the largest are detected as the reflection point pt instead of the peak pn where disturbance and the like may be included. Therefore, there is a case where the peak pn matches the reflection point pt at one time, and there is a case the peak pn doesn't match the reflection point pt at one time, as shown in FIG. 7A or FIG. 7B. By performing the above generation process, primary correction, and secondary correction, peaks caused by disturbance such as multipath can be removed.

For the other blocks, the data correction unit 44 performs the same generation process, primary correction, and secondary correction for each of the other blocks in the same manner as described above. As described above, in the $m^{th}$ block Bm, the data correction unit 44 per forms generation process and a correction process including the primary correction and the secondary correction. The generation process in the $m^{th}$ block Bm includes generating the approximate C based on distance components of signal strength at a peak pn of a plurality of distance-based fluctuation data of the first to $N^{th}$ distance-based fluctuation data, the plurality of distance-based fluctuation data included in the $m^{th}$ block Bm. The correction process in in the $m^{th}$ block Bm includes correcting distance components of the plurality of distance-based fluctuation data so that the approximate line C approaches a reference value set for the block Bm. The data correction unit 44 performs the generation process, the primary correction, and the secondary correction for each of the first to $M^{th}$ blocks.

In the generation process, the primary correction, and the secondary correction for each block, a reference value arbitrarily set fir each block may be used. For example, a position of a peak in first distance-based fluctuation data in each block may be set as a reference value in the block. For this reason, after performing the generation process, the primary correction, and the secondary correction in each of the plurality of blocks, the positions of reference values deviate from each other between the plurality of blocks. Therefore, the data correction unit 44 may perform tertiary correction. In the tertiary correction, the data correction unit 44 translates (performs parallel shift of) distance components of a plurality of distance-based fluctuation data included in each block along the distance axis so that the positions of the reference values between the plurality of blocks match each other. In the tertiary correction, the data correction unit 44 may adopt a reference value in the first block B1 as a reference value for all the blocks.

Figure 5B:
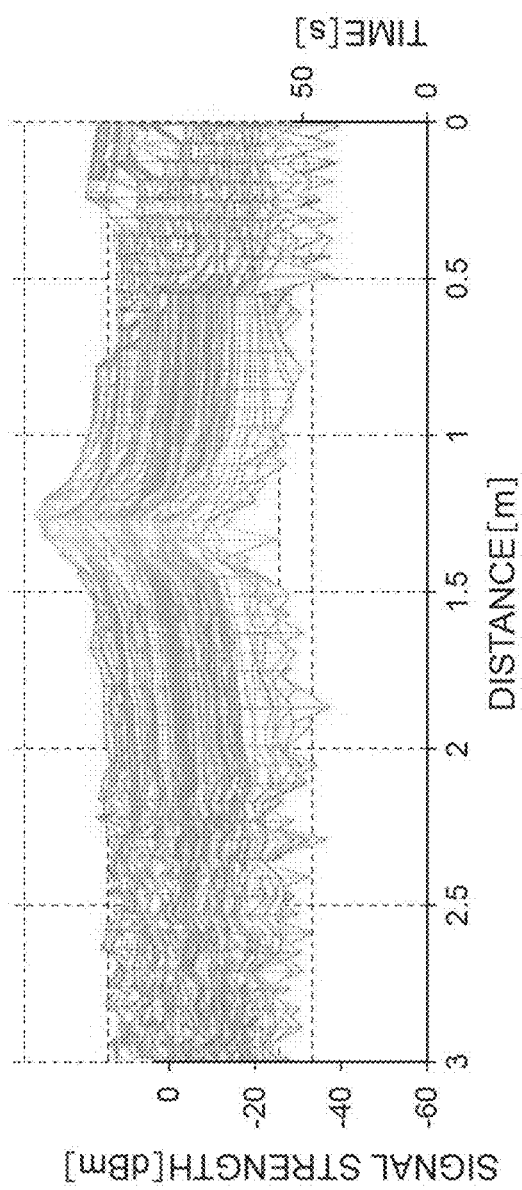
FIG. 5B is a diagram showing an example of corrected time-series data.

As described above, through the generation process, the primary correction, the secondary correction, and the tertiary correction, as shown in FIG. 5B, corrected time-series data in which the living body H seems to be stationary at the reference value can be obtained. In addition, in FIG. 6A and the like, the position of the reference value is set to x=0 for simplicity of explanation, but in the examples shown in FIGS. 5A and 5B, the position of the reference value in the first block is around 1.3 m, and peaks and reflection points from the detection part are arranged on around 1.3 m.

Figure 8:
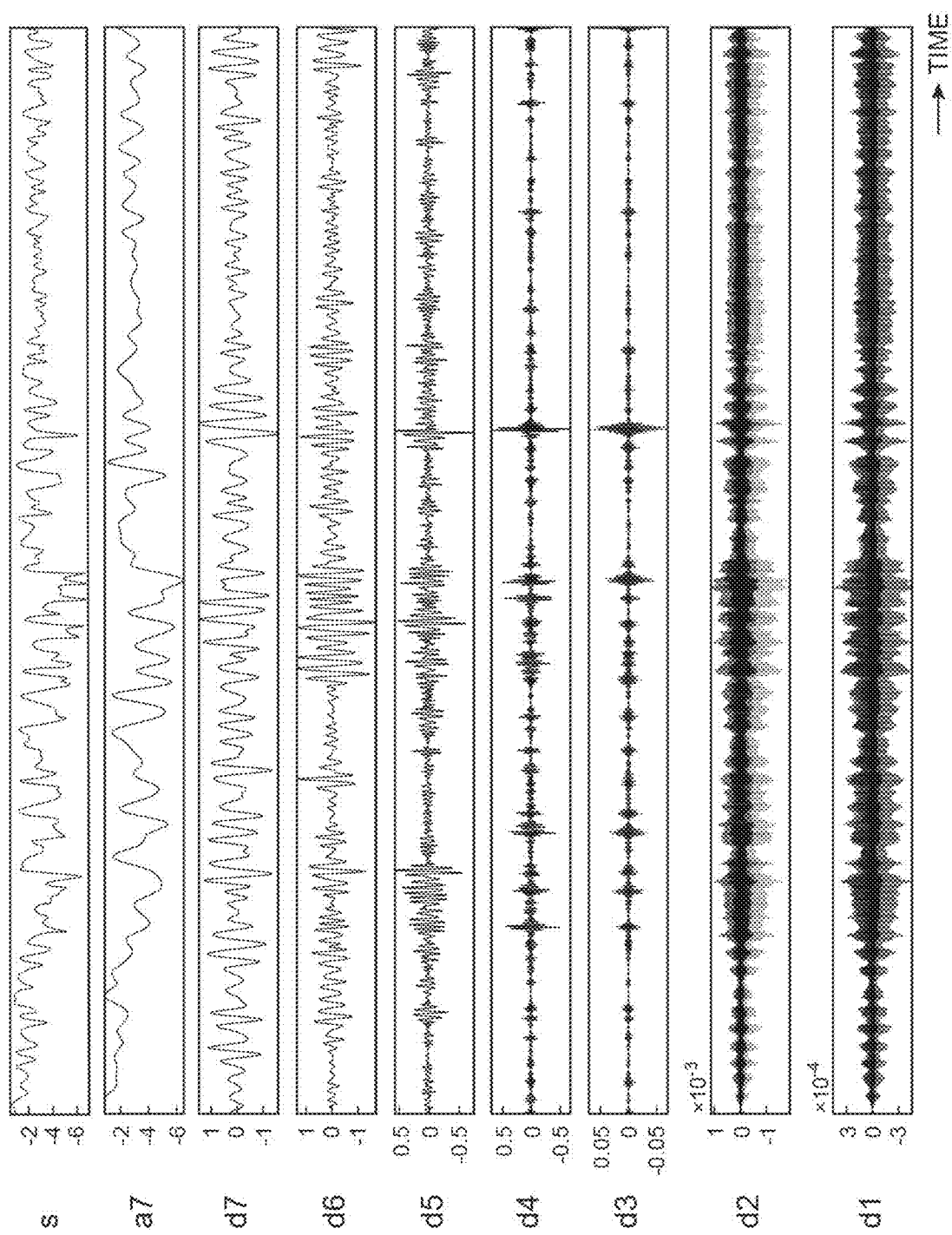
FIG. 8 shows graphs for describing the decomposition of by multiple resolution analysis.

The fluctuation data generation unit 45 has a function of performing strength obtaining process. The strength obtaining process includes obtaining one corresponding strength information which is a signal strength included in the $n^{th}$ distance-based fluctuation data and based on reflected waves from a predetermined detection part of the living body H. For example, the fluctuation data generation unit 45 generates time-based fluctuation data in which a plurality of corresponding strength information are arranged in time series by performing the strength obtaining process on the first to $N^{th}$ distance-based fluctuation data included within a predetermined time. For example, the fluctuation data generation unit 45 may obtain, as time-based fluctuation data, a set of signal strengths arranged in time series at the reference value (as an example, a reference value for the first block B1) in the corrected time-series data. The time-based fluctuation data indicates temporal change in signal strength in accordance with the reflected waves from the detection part. The signal indicated by "s" in FIG. 8 shows an example of the time-based fluctuation data generated by the fluctuation data generation unit 45. By performing the correction process by the data correction unit 44, influences of a movement (movement or micro-movement) of the living body H are reduced in the time-based fluctuation data. The time-based fluctuation data includes biological information (respiration information and pulsation information) of the detection part of the living body H.

The biological data generation unit 46 has a function of generating the biological data of the detection part of the living body H. The biological data generation unit 46 may generate the biological data of the detection part of the living body H, for example, by performing multiple resolution analysis multi-resolution analysis) on the time-based fluctuation data. In the multiple resolution analysis on the time-based fluctuation data, the biological data generation unit 46 repeats wavelet transform to decompose the time-based fluctuation data into a high-frequency component (high-resolution component) and a low-frequency component (low-resolution component). The resolution level in the multiple resolution analysis may be, for example, about 5 to 10 or may be about 7. The biological data generation unit 46 may perform wavelet transform by using, for example, a Haar wavelet, a Daubechies wavelet, a Symlet wavelet, or a Coiflet wavelet as a wavelet function or a basis function.

An example of multiple resolution analysis on time-based fluctuation data will be specifically described. FIG. 8 shows examples of a plurality of signals (eight signals) obtained by decomposing the time-based fluctuation data indicated by "s" FIG. 8 using multiple resolution analysis. Hereinafter, each of the plurality of signals decomposed by multiple resolution analysis referred to as "decomposed signal". First, the biological data generation unit 46 decomposes the time-based fluctuation data into a high-frequency component and a low-frequency component by performing first wavelet transform on the time-based fluctuation data. The high-frequency component decomposed at the first wavelet transform is a decomposed signal indicated by "d1" in FIG. 8. The biological data generation unit 46 performs second wavelet on the low-frequency component decomposed in the first wavelet transform. The high-frequency component decomposed at the first wavelet transform is a decomposed signal indicated by "d2" in FIG. 8.

The biological data generation unit 46 repeats third and subsequent wavelet transforms in the same manner. In this example, the time-based fluctuation data are decomposed into eight levels (frequency bands) by performing seven wavelet transforms. Decomposed signals indicated by "d3" to "d7" in FIG. 8 are high-frequency components decomposed by the third to seventh wavelet transforms, respectively. The decomposed signals indicated by "a7" in FIG. 8 is a low-frequency component decomposed by the seventh wavelet transform.

The biological data generation unit 46 extracts at least one of a pulsation signal and a respiration signal from a plurality of decomposed signals. The pulsation signal is a component corresponding to (in accordance with) the pulsation of the living body H included in the time-based fluctuation data. The respiration signal is a component corresponding to (in accordance with) the respiration of the living body H included in the time-based fluctuation data. For example, the biological data generation unit 46 may extract a decomposed signal, as a respiration signal, having a frequency range (for example, 0.5 Hz or less) corresponding to the respiration from the plurality of decomposed signals. The biological data generation unit 46 may extract a decomposed signal, as a pulsation signal, having a frequency range (for example, 0.8 Hz to 1.6 Hz) corresponding to the pulsation from the plurality of decomposed signals.

In the example shown in FIG. 8, the biological data generation unit 46 may extract the decomposed signal indicated by "a7" in FIG. 8 as a respiration signal. The biological data generation unit 46 may extract the decomposed signal indicated by "d7" in FIG. 8 as a pulsation signal. When the frequency range of a plurality of decomposed signals (for example, the two decomposed signals indicated by "d6" and "d7" in FIG. 8) corresponds to a frequency range corresponding to the pulsation (respiration), the biological data generation unit 46 may recombine the plurality of decomposed signals and extract a recombined signal as a pulsation signal (respiration signal). When executing recombination, the biological data generation unit 46 may generate the recombined signal by adding up the plurality of decomposed signals. The biological data generation unit 46 may separate the respiration signal and the pulsation signal from the time-based fluctuation data by using an independent component analysis method or a moving average difference method instead of the multiple resolution analysis.

When extracting the pulsation signal from the plurality of decomposed signals, the biological data generation unit 46 may exclude an extra signal corresponding to (in accordance with) the movement of the living body H different from the pulsation. Hereinafter, a signal corresponding to the movement of the living body H different from the pulsation referred to as a "non-pulsation signal". Examples of the movement of the living body H different from the pulsation include a periodic movement other than the pulsation caused by the living body H itself and a periodic movement occurring in the living body H due to an external factor. An example of the former includes a respiratory movement of the living body H. An example of the latter includes vibration that acts on the living body H from a vehicle, on which the living body H rides, with the driving of the vehicle. The biological data generation unit 46 may exclude a non-pulsation signal from the plurality of decomposed signals when extracting a pulsation signal. The biological data generation unit 46 may extract, as a pulsation signal, a signal obtained by recombining a plurality of remaining decomposed signals after the non-pulsation signal is excluded. For example, the biological data generation unit 46 may exclude, as a pulsation signal, a signal obtained by excluding the decomposed signal indicated by "a7" in FIG. 8 corresponding to the respiratory movement of the living body H. Then, the biological data generation unit 46 may recombine the remaining signals indicated by "d1" to "d7" after the signal indicated by "a7" is excluded.

Figure 9:
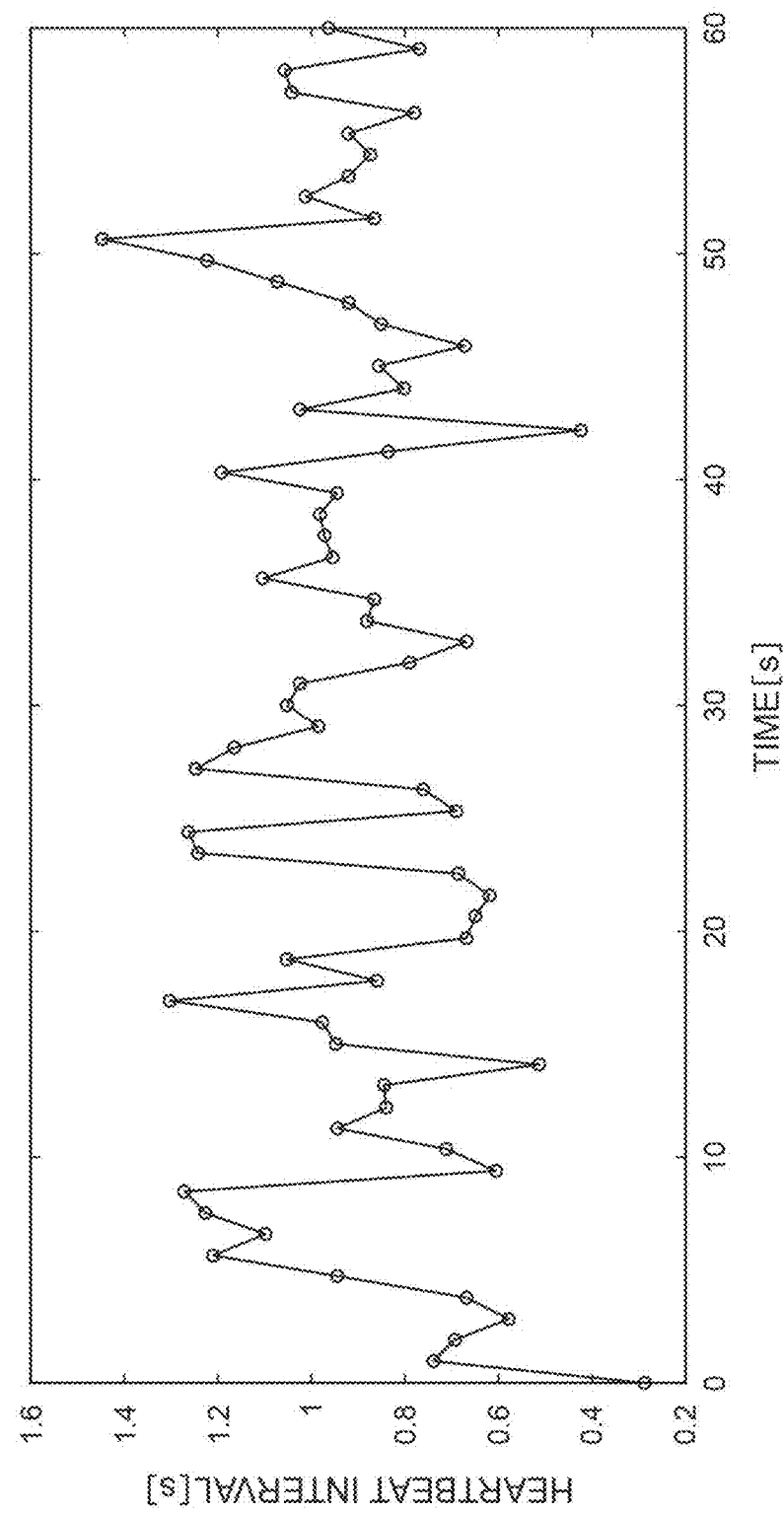
FIG. 9 is a graph showing an example of heartbeat interval data.

As shown in FIG. 9, the biological data generation unit 46 may generate heartbeat interval data indicating temporal change in heartbeat interval (RR interval: RRI), as biological data, by calculating the time interval between adjacent points of a plurality of maximal values included in the pulsation signal. When generating the heartbeat interval data from the pulsation signal, the biological data generation unit 46 may perform spectral analysis on the pulsation signal in order to calculate the heartbeat interval with high accuracy. For example, the biological data generation unit 46 may spectrally analyze on the pulsation signal using autoregressive model (AR model). In the spectral analysis using the AR model, the biological data generation unit 46 may calculate parameters (coefficients) of the AR model by using the Berg method, and may determines an order of the AR model by using the Akaike's information criterion (AIC).

The biological data generation unit 46 may calculate the heartbeat interval data from the pulsation signal from which a noise component has been removed by the spectral analysis using the AR model. Based on the heartbeat interval data calculated in this manner, the biological data generation unit 46 may calculate the number of heartbeats per unit time (heart rate, average heart rate) as biological data. The biological data generation unit 46 may calculate the number of breaths per unit time (for example, one minute) or respiratory rate as biological data in the same manner as described above. The biological data generation unit 46 may perform spectral malysis by using a Maximum Entropy Method (MEM) or a MemCalc analysis system instead of the AR model.

The biological data obtaining device 20 may have a function of outputting the biological data (for example, heartbeat interval data) generated by the biological data generation unit 46 to the outside. The biological data obtaining system 1 may include, fir example, an alarm device, and the biological data obtaining device 20 may output biological data to the alarm device. The biological data obtaining device 20 may transmit some data to an alarm device, which is provided in a place (building) different from a place where the transmitting and receiving device 10 and the biological data obtaining device 20 are provided, through the communication device 23. The biological data obtaining device 20 may store the obtained biological data in the storage unit 43.

Method of Obtaining Biological Data

Subsequently, a biological data obtaining method will be described with reference to FIG. 10. An example case where information relating to the pulsation of the living body H (temporal change in heartbeat interval) is obtained as biological data will be described.

First, the instruction processing unit 31 of the transmitting and receiving device 10 (control unit 14) instructs the transmitter 11 to transmit radio waves from the transmitter 11 toward the detection region R. Then, the instruction processing unit 31 receives reception data based on the reflected waves of the radio waves through the receiver 12, and outputs the reception data to the communication device 13. Then, the instruction processing unit 31 instructs the communication device 13 to transmit the reception data to the communication device 23 of the biological data obtaining device 20.

Next, the data obtaining unit 41 of the biological data obtaining device 20 (control unit 24) obtains the reception data transmitted to the communication device 23 as reception data at time t1. The data obtaining unit 41 outputs the obtained reception data at time t1 to the signal strength calculation unit 42.

Figure 10:
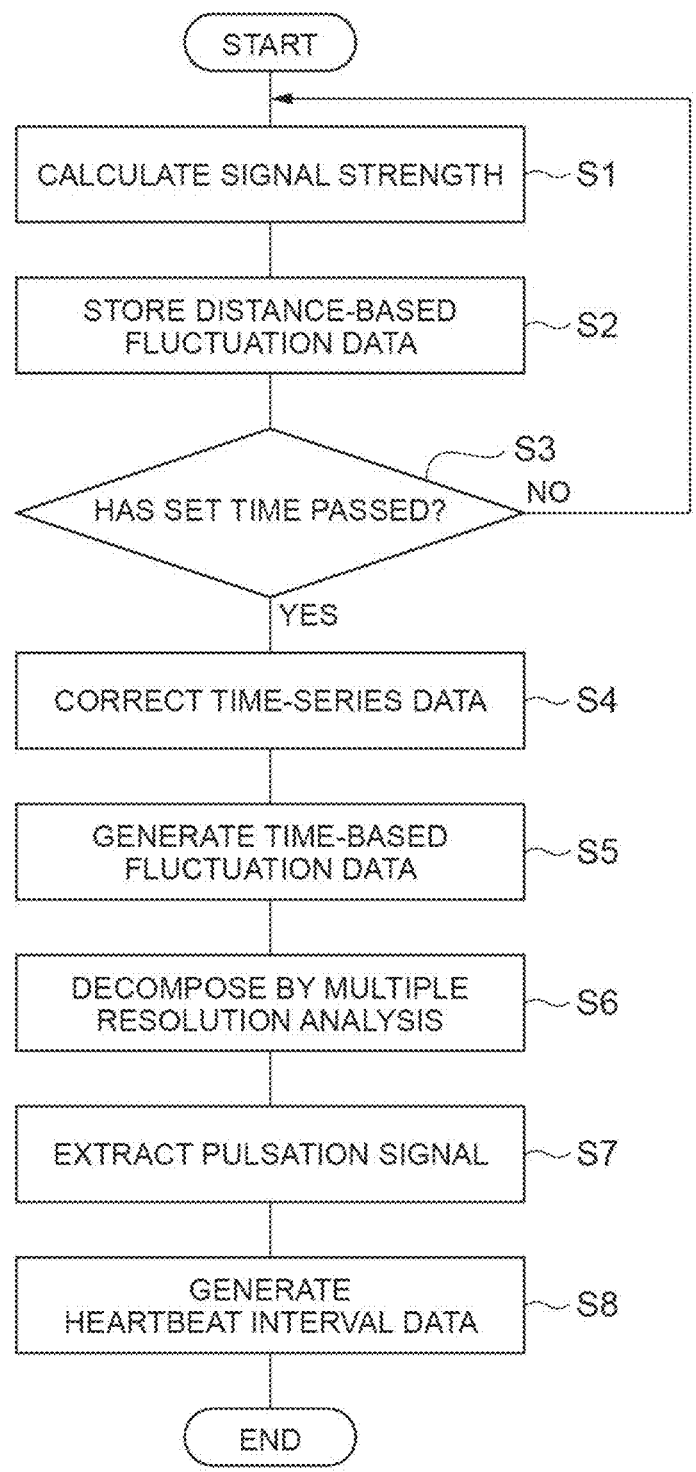
FIG. 10 is a flowchart for describing a procedure for obtaining biological data.

Next, the signal strength calculation unit 42 calculates first distance-based fluctuation data indicating variation (fluctuation) of signal strength with respect to distance based on the reception data at time t1 (step S1 in FIG. 10). The signal strength calculation unit 42 may calculate the first distance-based fluctuation data after performing difference process on the reception data by using reference reception data which are data based on reflection of the radio waves when the living body H is not present in the detection region R. The signal strength calculation unit 42 outputs the calculated first distance-based fluctuation data to the storage unit 43.

Next, the storage unit 43 stores the first distance based fluctuation data (step S2 in FIG. 10). Then, the control unit 24 determines whether or not the set time has passed from an initial time (step S3 in FIG. 10). When it is determined that the set time has not passed (step S3: NO), the control unit 24 repeats steps S1 to S3. As a result, the first to $N^{th}$ distance-based fluctuation data are stored in the storage unit 43 in the set time.

When it is determined that the set time has passed (step S3: YES), the data correction unit 44 corrects the time-series data (the first to $N^{th}$ distance-based fluctuation data) stored in the storage unit 43 (step S4 in FIG. 10). For example, the data correction unit 44 performs correction process which includes correcting distance components of the $n^{th}$ distance-based fluctuation data so that a distance component (a reflection point from the detection part) corresponding to the detection part in the $n^{th}$ distance-based fluctuation data approaches a reference value. The data correction unit 44 generates corrected time-series data by performing the correction process on the first to $N^{th}$ distance-based fluctuation data (see FIGS. 5A and 5B). The data correction unit 44 may generate corrected time-series data by performing the primary correction, the secondary correction, and the tertiary correction as in the examples shown in FIGS. 6A, 6B, 7A, and 7B. The data correction unit 44 outputs the corrected time-series data to the fluctuation data generation unit 45.

Next, the fluctuation data generation unit 45 generates time-based fluctuation data based on the corrected time-series data (step S5 in FIG. 10). For example, the fluctuation data generation unit 45 performs strength obtaining process which includes obtaining one corresponding strength information. The one corresponding strength information is a signal strength included in the $n^{th}$ distance-based fluctuation data and based on reflected waves from the detection part of the living body H. The fluctuation data generation unit 45 generates time-based fluctuation data in which the corresponding strengths are arranged in time series by performing the strength obtaining process on the first to $N^{th}$ distance-based fluctuation data. The fluctuation data generation unit 45 may obtain, as time-based fluctuation data, a set of signal strengths arranged along the reference value in the corrected time-series data (see FIGS. 5B and 8). The reference value may be set for each of operation to obtain the biological data. The fluctuation data generation unit 45 outputs the generated time-based fluctuation data to the biological data generation unit 46.

Next, the biological data generation unit 46 performs multiple resolution analysis on the time-based fluctuation data (step S6 in FIG. 10). The biological data generation unit 46 generates a plurality of decomposed signals (see FIG. 8) having different frequency ranges from the time-based fluctuation data by repeating wavelet transform which includes decomposing a signal (or data) into high-frequency components and low-frequency components to decompose.

Next, the biological data generation unit 46 extracts a pulsation component from the plurality of decomposed signals (step S7 in FIG. 10). For example, the biological data generation unit 46 may extract a decomposed signal, as a pulsation signal indicating a pulsation component, having a frequency range (for example, 0.8 Hz to 1.6 Hz) corresponding to the pulsation from the plurality of decomposed signals. When the frequency range of a plurality of decomposed signals corresponds to the frequency range corresponding to the pulsation, the biological data generation unit 46 may recombine the plurality of decomposed signals to extract the recombined signal as a pulsation signal.

Next, the biological data generation unit 46 generates heartbeat interval data based on the pulsation signal (step S8 in FIG. 10). For example, the biological data generation unit 46 may generate heartbeat interval data as biological data by repeating calculation of time interval between adjacent points each of which is maximal point in the pulsation signal (see FIG. 9). When generating the heartbeat interval data from the pulsation signal, the biological data generation unit 46 may perform spectral analysis on the pulsation signal in order to calculate the heartbeat interval with high accuracy. For example, the biological data generation unit 46 may calculate the heartbeat interval data from the pulsation signal from which a noise component has been removed by the spectral analysis using the AR model.

The biological data Obtaining device 20 may output the heartbeat interval data generated by the biological data generation unit 46 to the outside (for example, an external alarm). The biological data obtaining device 20 may store the heartbeat interval data generated by the biological data generation unit 46 in the storage unit 43. The biological data obtaining device 20 (control unit 24) may repeatedly obtain time-series data (first to $N^{th}$ distance-based fluctuation data) for each set time by repeating steps S1 to S3 after the end of the first set time in step S3. The biological data obtaining device 20 may calculate the heartbeat interval data for each set time by repeating a series of processes of steps S4 to S8. A series of processes of steps S4 to S8 performed in one set time may be performed in parallel with the processes of steps S1 to S3 performed in another set time.

When measuring heartbeat data of the user by using the above-mentioned wearable device, it is necessary to perform the measurement in a state in which the measurement device is in contact with the user. Therefore, it takes time and effort to attach and detach the measurement device during measurement, and there is a concern that the wearing of the measurement device may cause discomfort to the user. For this reason, a technique for measuring biological data, such as heartbeat data, in a non-contact manner by using a radio wave sensor or the like has been studied. However, when trying to measure biological data in a non-contact manner by using a radio wave sensor or the like, if a living body (for example, a human body, an animal, or the like) whose biological data is to be measured moves, the movement may affect the obtaining of biological data based on the reflected waves from the living body.

In some examples, the first to $N^{th}$ distance-based fluctuation data which are a number of data sets obtained from the reflected waves within the set time are stored in the storage unit 43 as time-series data. Then, from the time-series data, time-based fluctuation data in which the signal strength information that are signal strengths based on the reflected waves from the detection part are arranged in time series may be Obtained. Since signal strengths, included in the time-based fluctuation data, are based on the reflected waves from the detection part of the living body H, even if the living body H that is a detection target moves, the biological data can be obtained based on the signal strengths in accordance with the reflected waves from the detection part. As a result, it is possible to accurately detect biological data in a non-contact manner.

There is another method of obtaining time-based fluctuation data without considering the movement under the condition that the living body H that is a detection target is moving. In the another method, a reflection position from the living body H at a predetermined reference time is specified, and the position is set as a measurement position (reference value) to extract temporal change in signal strength at the measurement position. In this method, since there is a period in which the information of the detection part is not included at the measurement position due to the movement of the living body H, it is difficult to accurately detect the biological information due to the movement. On the other hand, in the examples described above, the corrected time-series data is obtained by performing correction process, which includes correcting distance components of the $n^{th}$ distance-based fluctuation data so that a distance component (range bin) corresponding to the detection part in the $n^{th}$ distance-based fluctuation data approaches the reference value, on the first to $N^{th}$ distance-based fluctuation data. Then, when executing the strength obtaining process, the fluctuation data generation unit 45 obtains signal strengths at the reference value from the corrected time-series data as corresponding strength information. In this case, the movement of the living body H appears in the variation of distance components at a peak of signal strength, and the distance component corresponding to the detection part near the peak is corrected so as to approach the reference value, so that the movement of the living body H is corrected in time-series data. Therefore, time-based fluctuation data of signal strengths in which the influence of the movement of the living body H is reduced is obtained, and the biological data is obtained based on the time-based fluctuation data. As a result, even if the living body H moves, it is possible to accurately detect the biological data of the living body.

In some examples, the correction process includes correcting the distance components of $p^{th}$ to $q^{th}$ of the first to $N^{th}$ distance-based fluctuation data distance-based fluctuation data so that the approximate line approaches the reference value, the $p^{th}$ to $q^{th}$ distance-based fluctuation data are included within the predetermined time, the approximate line is obtained based on distance components of signal strength at a peak of the $p^{th}$ to $q^{th}$ distance-based fluctuation data. The movement trajectory of the living body H can be expressed by the approximate line of the distance components at the peaks included in the distance-based fluctuation data. Therefore, even if the distance-based fluctuation data includes a peak due to disturbance such as multipath, the peak can be excluded because the peak is far from the approximate line. As a result, it is possible to more reliably detect biological data with high accuracy.

In some examples, the correction process includes performing block correction process on the first to $M^{th}$ blocks B1 to BM obtained by sequentially dividing the time-series data in time series, the block correction process includes correcting distance components of a plurality of distance-based fluctuation data of the pieces of first to $N^{th}$ distance-based fluctuation data so that the approximate line approaches an arbitrary reference value set for each of the first to $M^{th}$ blocks B1 to BM, the plurality of distance-based fluctuation data are included in the $m^{th}$ block Bm of the first to $M^{th}$ blocks, and the approximate line is Obtained based on distance components of signal strength at a peak of the plurality of distance-based fluctuation data. In this case, since the approximate line showing the movement trajectory of the living body H is calculated for each block, the approximate line can be made closer to the movement trajectory of the living body H. Therefore, it is possible to detect biological data more accurately.

In some examples, the biological data generation unit 46 is configured to generate the biological data of the detection part of the living body H by performing multiple resolution analysis on the time-based fluctuation data. In this case, the signal in the frequency range corresponding to the biological data is extracted from the time-based fluctuation data by the multiple resolution analysis. Therefore, even if components other than the biological data are included in the time-based fluctuation data, the biological data can be obtained.

In some examples, the biological data generation unit 46 is configured to decompose the time-based fluctuation data into a plurality of decomposed signals by performing multiple resolution analysis on the time-based fluctuation data and generate pulsation data relating to the pulsation of the living body H based on the pulsation signal of the plurality of decomposed signals, the pulsation signal corresponds to the pulsation of the living body H. In this case, the signal in the frequency range corresponding to the pulsation is extracted from the time-based fluctuation data by the multiple resolution analysis. Therefore, even if components other than the pulsation of the living body H are included in the time-based fluctuation data, the pulsation data can be obtained.

In some examples, the biological data generation unit 46 is configured to generate heartbeat interval data indicating temporal change in the heartbeat interval of the living body H by spectrally analyzing the pulsation signal using the AR model. In this case, since noise included in the pulsation signal is removed by performing the spectral analysis using the AR model on the pulsation signal, it is possible to accurately detect the heartbeat interval.

In some examples, the receiver 12 may oversample the reflected wave based on a reference frequency corresponding to the pulsation of the living body H. The first to $N^{th}$ distance-based fluctuation data calculated by the signal strength calculation unit 42 based on the reception data output from the receiver 12 may be data obtained by oversampling the reflected wave based on the reference frequency corresponding to the pulsation of the living body H. In this case, since the sampling period becomes short and accordingly more data can be obtained, it is easy to extract the pulsation signal from the time-based fluctuation data.

In some examples, the biological data generation unit 46 is configured to generate heartbeat interval data after excluding an extra signal of the plurality of decomposed signals, the extra signal corresponds to a movement of the living body H different from the pulsation. In this case, since the information due to the movement of the living body H different from the pulsation is excluded from the time-based fluctuation data, it is possible to accurately detect the pulsation data.

In some examples, the communication device 13 configured to transmit the reception data in accordance with the reflected wave to the biological data obtaining device 20 by using wireless communication is provided. Capacity of the control unit (memory) that is mounted in the transmitting and receiving device 10 for transmitting the radio waves and receiving the reflected waves may be small, but a large amount of data can be handled by performing data storage and processing in the separate biological data obtaining device 20. Therefore, it is possible to continue the detection of biological data for a long time.

It is to be understood that not all aspects, advantages and features described herein may necessarily be achieved by, or included in, any one particular example. Indeed, having described and illustrated various examples herein, it should be apparent that other examples may be modified in arrangement and detail.

In some examples, the transmitting and receiving device 10 (communication device 13) and the biological data obtaining device 20 (communication device 23) may be communicably connected to each other by wire.

In some examples, the biological data obtaining device 20 and the transmitting and receiving device 10 may be installed in the same building. Or the biological data obtaining device 20 and the transmitting and receiving device 10 may be installed in different buildings from each other. Examples of a building in which biological data obtaining device 20 is installed include a house of a family living separately from the living body H, a facility that provides health management services, a facility that provides emergency medical services (fire department in Japan), and a hospital. In these cases, it is possible to know the state of the living body H even at a location away from the living body H. For this reason, even if the living body H lives alone, it is possible to monitor the state of the living body H. The biological data obtaining device 20 may have a function of estimating the state (fro example, presence or absence of abnormality, health state) or the like of the living body H from the obtained biological data.

Figure 11:
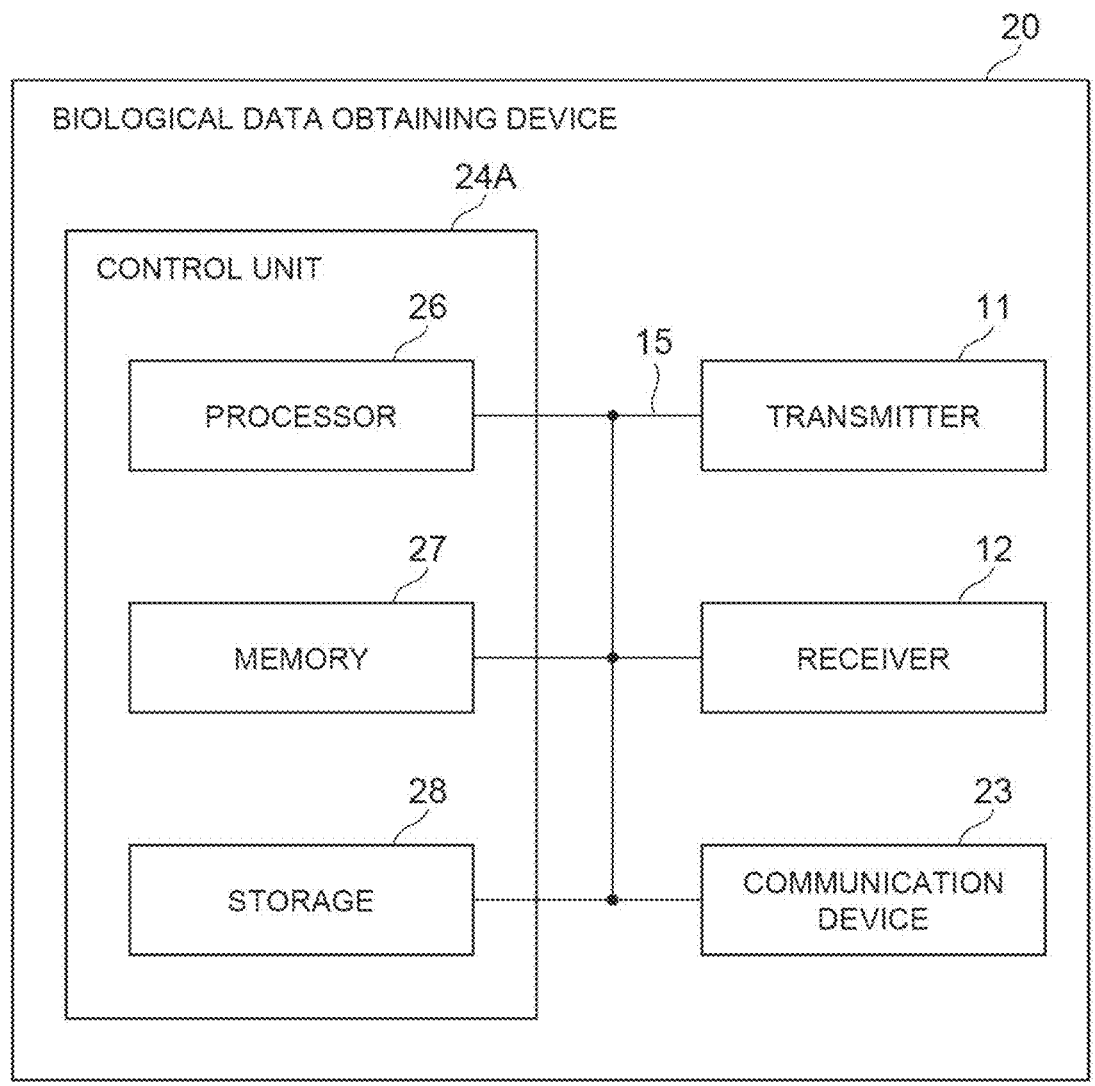
FIG. 11 is a block diagram schematically showing another example of a biological data obtaining device.
Figure 12:
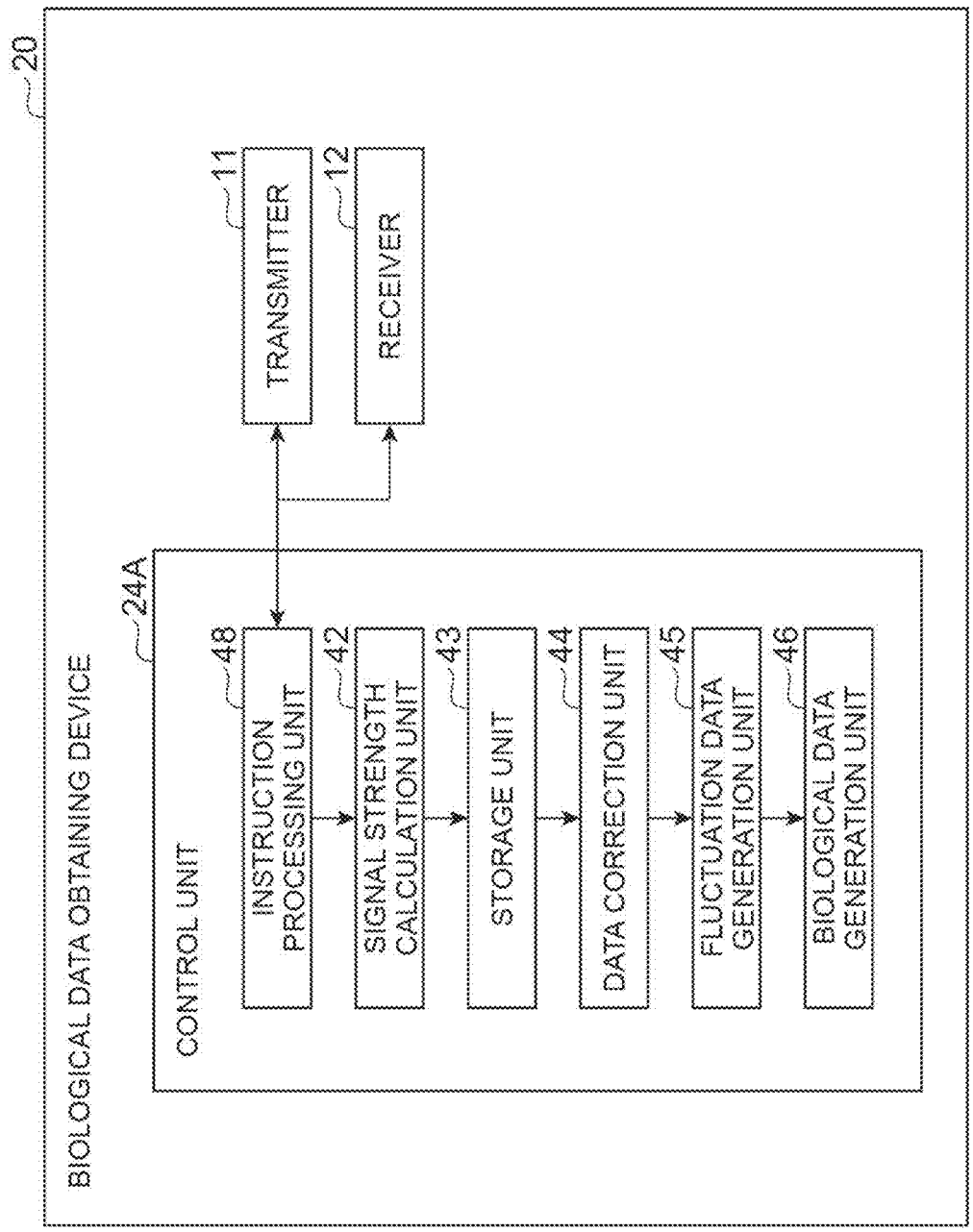
FIG. 12 is a block diagram schematically showing another example of a biological data obtaining system.

In some examples, instead of the biological data obtaining system 1, as shown in FIG. 11, the biological data Obtaining device 20 may further include the transmitter 11 and the receiver 12. In other words, the transmitter 11 and the receiver 12 for transmitting and receiving radio waves may be installed in the device for obtaining biological data (biological data obtaining device 20). The biological data obtaining device 20 shown in FIG. 11 is different from the biological data obtaining device 20 shown in FIG. 3 in that the biological data obtaining device 20 shown in FIG. 11 includes a control unit 24A, the transmitter 11, and the receiver 12. The control unit 24A has a function of controlling the transmitter 11 and the receiver 12, and is different from the control unit 24 in that the control unit 24A includes an instruction processing unit 48 instead of the data obtaining unit 41 as shown in FIG. 12. The instruction processing unit 48 may have the same function as the function of the instruction processing unit 31. In the biological data obtaining system 1 including the biological data obtaining device 20 shown in FIG. 11, not the transmitting and receiving device 10 separate from the biological data obtaining device 20 but the biological data obtaining device 20 itself has a function of transmitting and receiving radio waves. Therefore, the system can be simplified.

In some examples, the transmitter 11 and the receiver 12 may be configured as separate devices. For example, the biological data obtaining system 1 may include a transmitting device including the transmitter 11 and one controller and a receiving device having the receiver 12 and another control unit, instead of the transmitting and receiving device 10. The transmitting device, the receiving device, and the biological data obtaining device 20 may be communicably connected to each oilier wirelessly or by wire. In the transmitter 11, the receiver 12, and the instruction processing unit 48, Multiple input Multiple Output (MIMO) radar technology in which a plurality of antenna elements are disposed for both transmission and reception may be used.

Figure 13:
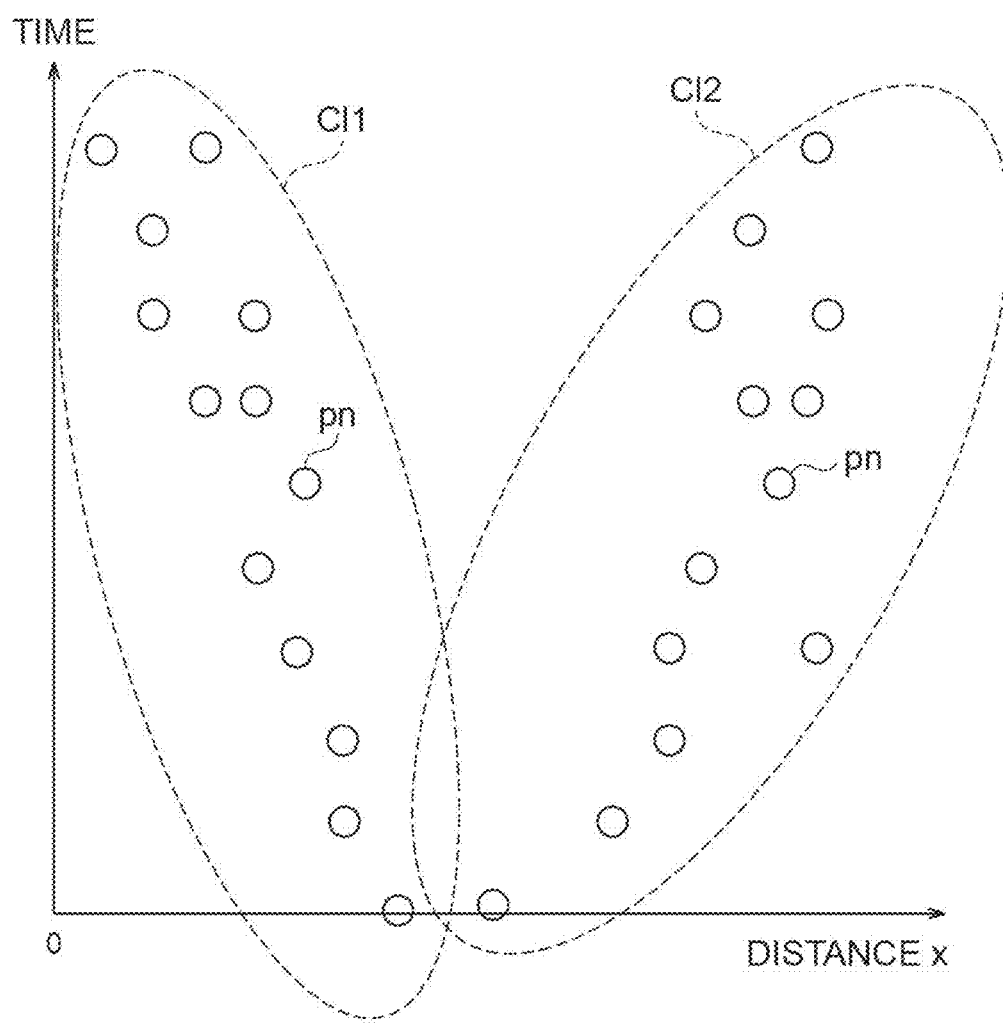
FIG. 13 is a diagram for describing a method of obtaining biological data when a plurality of living bodies are present in a detection region.

In some examples, the biological data obtaining device 20 may obtain respectively biological data (heartbeat interval data) for a plurality of living bodies H. A plurality of living bodies H (for example, two detection target persons) may be present in the detection region R. For example, considering a case where one detection target person moves away from the transmitting and receiving device 10 and the other detection target person approaches the transmitting and receiving device 10, a plurality of peaks par (scattering points) obtained from the distance-based fluctuation data are shown as two scattering point groups C11 and C12 (information of signal strength and distance) as shown in FIG. 13.

In some examples, when the data correction unit 44 detects that a plurality of scattering point groups are present in one block (a plurality of persons are present in one block), the data correction unit 44 may cluster each of the plurality of scattering point groups. The data correction unit 44 may generate corrected time-series data one by one for each of clustered scattering point groups by performing primary correction, secondary correction, and tertiary correction for each cluster. The fluctuation data generation unit 45 may generate time-based fluctuation data from the corrected time-series data obtained for each of clustered scattering point groups. The biological data generation unit 46 may generate biological data from the time-based fluctuation data obtained for each of clustered scattering point groups. After the biological data obtaining process for one detection target person is completed, biological data obtaining process for another detection target person may be performed.

An example of the biological data obtaining process when one living body H1 and another living body H2 are present in the detection region R will be described with reference to FIGS. 14 to 18. When the living bodies H1 and H2 are present in the detection region R, the signal strength calculation unit 42 may calculate the first to $N^{th}$ distance-based fluctuation data at times t1 to tN in time series order based on the reflected waves which are radio waves reflected from the living bodies H1 and H2. The radio waves reflected by the living bodies H1 and H2 include radio waves reflected only from the living body H1 and radio waves reflected only from the living body H2. The storage unit 43 may store time-series data including the first to N distance-based fluctuation data obtained based on the radio waves reflected from the living body and the living body H2. In addition to the above examples, the set time indicating the storage unit of the distance-based fluctuation data may be set in the range of several seconds to several tens of seconds. An example of the set time may be about 1 second to 180 seconds, or may be about 3 seconds to 120 seconds, or may be about 4 seconds to 60 seconds. Another example of the set time may be a time shorter than one second (for example, about several milliseconds to several hundred milliseconds).

Figure 14:
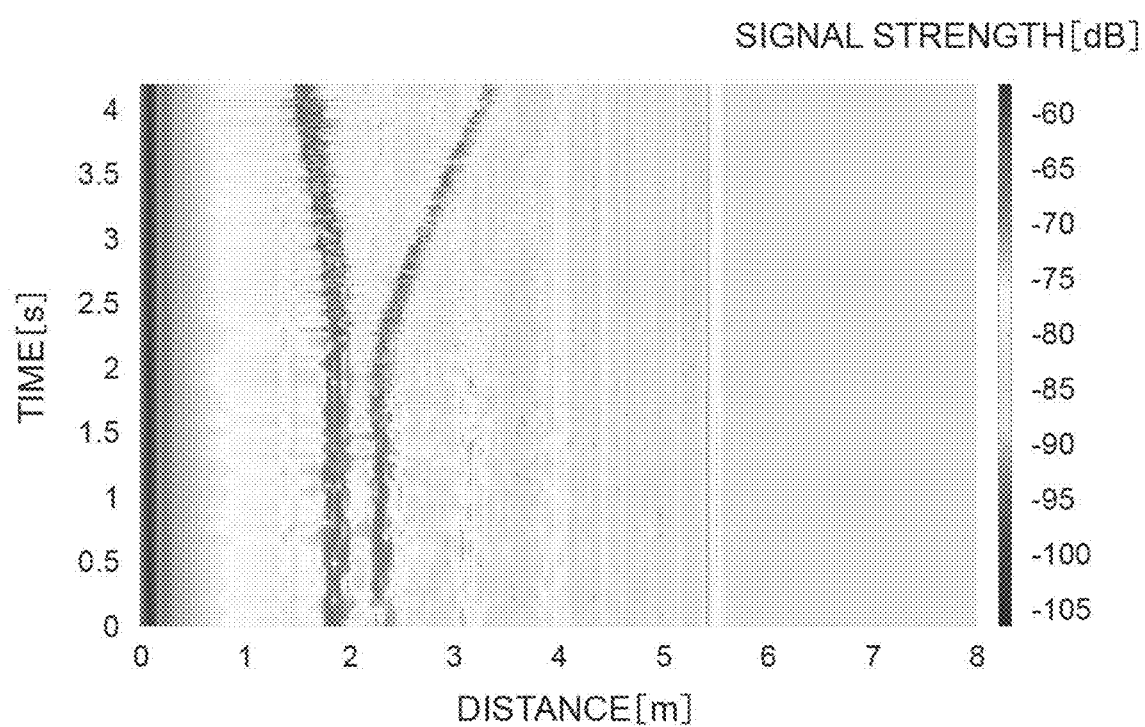
FIG. 14 is a diagram showing an example of time-series data when a plurality of living bodies are present in a detection region.

The time-series data shown in FIG. 14 includes a plurality of distance-based fluctuation data Obtained in about four seconds. The time-series data are data obtained in a measurement environment in which the living body H1 and the living body H2, who are subjects, face the transmitting and receiving device 10. More specifically, the time-series data are data obtained when measurement starts in a state in which the living body H1 is stationary at a location about 1.9 m away from the transmitting and receiving device 10 and the living body H2 is stationary at a location about 2.2 m away from the transmitting and receiving device 10 and after about two seconds from the start of the measurement, the living body H1 gradually approaches the transmitting and receiving device 10 and the living body H2 gradually moves away from the transmitting and receiving device 10.

The data correction unit 44 performs correction process for the living body H1 and correction process for the living body H2 based on the time-series data (first to $N^{th}$ distance-based fluctuation data for a predetermined time) stored in the storage unit 43. The data correction unit 44 may cluster a plurality of peaks pn (scattering points) in accordance with the number of detected living bodies by using a known method. For example, the data correction unit 44 may cluster a plurality of peaks pn for each living body by tracking the movement of each living body (each of the living body H1 and the living body H2) based on the change in signal strength at each range bin.

Figure 15A:
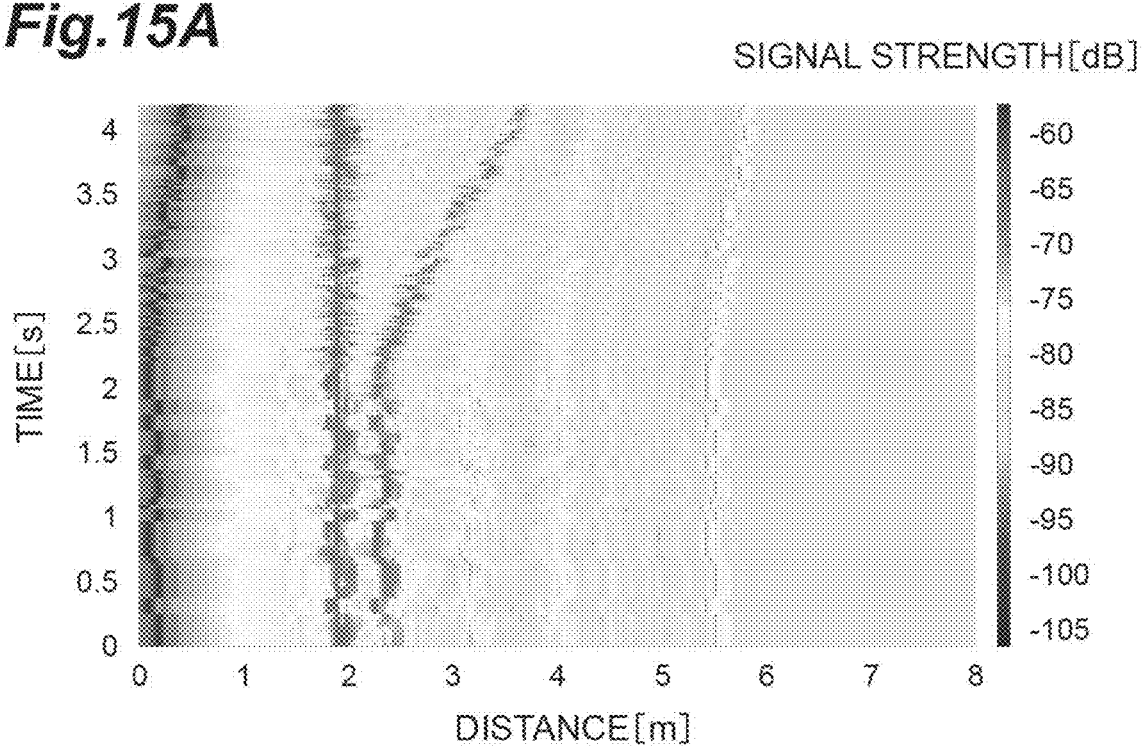
FIG. 15A is a diagram showing an example of corrected time-series data.
Figure 15B:
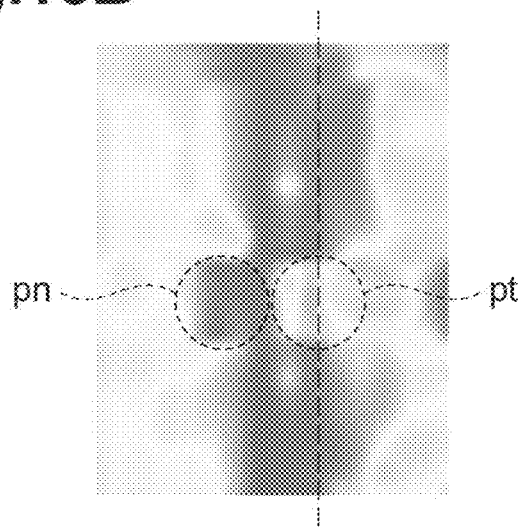
FIG. 15B is an enlarged view of a part of the time-series data shown in FIG. 15A.

For example, the data correction unit 44 may perform the above-described correction process which includes correcting distance components of the $n^{th}$ distance-based fluctuation data so that a distance component corresponding to the detection part of the living body in the $n^{th}$ distance-based fluctuation data approaches a reference value. FIG. 15A shows corrected time-series data obtained by performing the correction process based on a plurality of peaks pn clustered for the living body H1. In addition, as shown in FIG. 15B, by performing the secondary correction, the reflection point pt that does not match the peak pn is aligned with the reference value (position shown by the broken line) depending on the observation time.

The fluctuation data generation unit 45 may perform strength obtaining process which includes obtaining one corresponding strength information, the one corresponding strength information is a signal strength in the $n^{th}$ distance-based fluctuation data and based on the reflected waves from the detection part of the living body H1. The fluctuation data generation unit 45 may generate time-based fluctuation data in which the corresponding strength information are arranged in time series by performing the strength obtaining process associated with the living body on the first to $N^{th}$ distance-based fluctuation data. For example, the fluctuation data generation unit 45 may obtain, as time-based fluctuation data, a group of signal strengths arranged in time series at the reference value in the corrected time-series data relating to the living body H1.

Figure 16A:
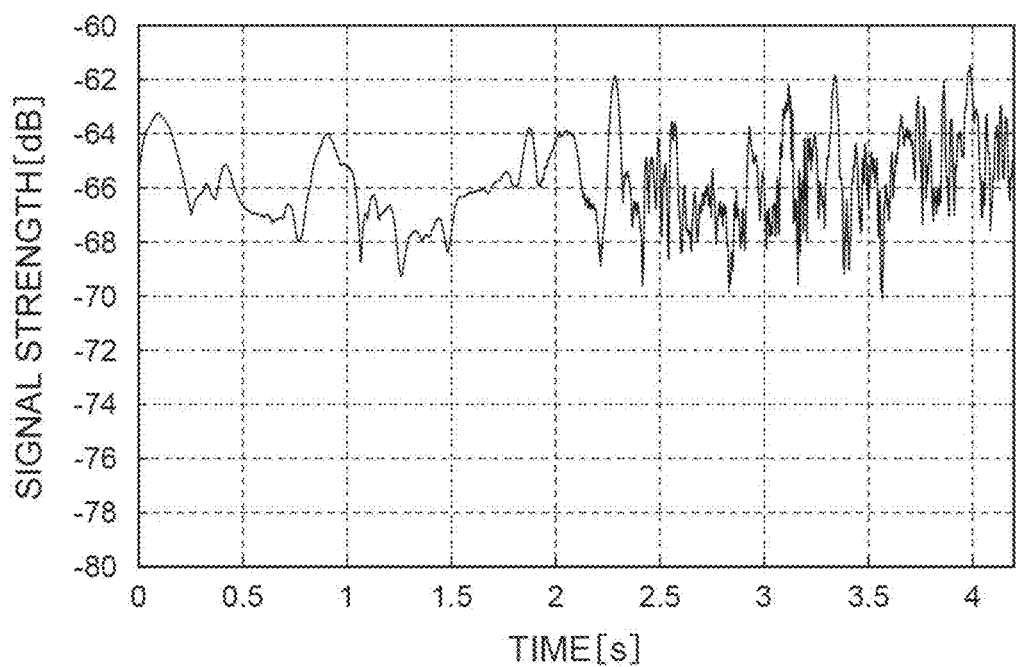
FIG. 16A is a graph showing a temporal change in signal strength obtained from time-series data that are not corrected.
Figure 16B:
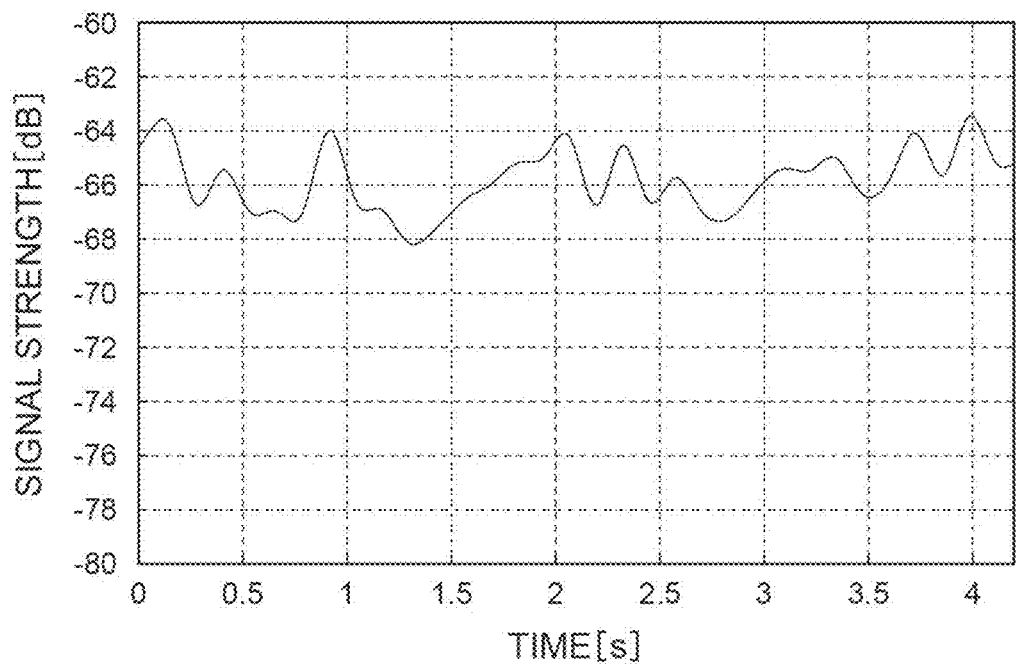
FIG. 16B is a graph showing a temporal change in signal strength obtained from corrected time-series data.

FIG. 16A shows temporal change in signal strength at a reference value (for example, the distance is 1.9 m) in the time-series data before correcting shown in FIG. 14. FIG. 16B shows temporal change in signal strength at the reference value in the corrected time-series data shown in FIG. 15A. In the temporal change in signal strength shown in FIG. 16A, signal strengths of reflected waves from the reflection position other than the detection part of the living body H1 are obtained from about two seconds after the start of the measurement. In the temporal change in signal strength shown in FIG. 16B, since the time-series data is corrected, signal strengths of reflected waves from the detection part of the living body H1 are continuously obtained.

Figure 17:
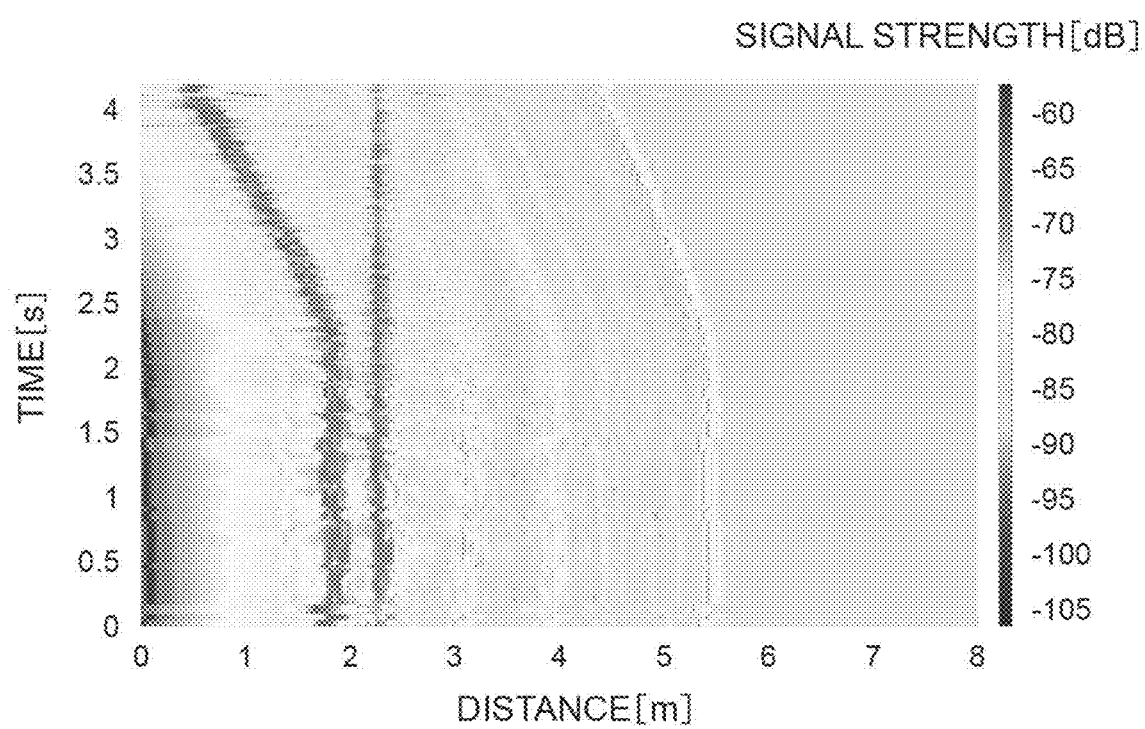
FIG. 17 is a diagram showing an example of corrected time-series data.

In addition to the correction process associated with the living body H1, the data correction unit 44 may perform correction process which includes correcting distance components of the $n^{th}$ distance-based fluctuation data so that a distance component corresponding to the detection part of the living body H2 in the $n^{th}$ distance-based fluctuation data approaches another reference value. FIG. 17 shows corrected time-series data obtained by performing the correction process based on a plurality of peaks pn clustered for the living body H2.

In addition to the strength obtaining process associated with the living body H1, the fluctuation data generation unit 45 may perform strength obtaining process which includes obtaining one corresponding strength information, the one corresponding strength information is a signal strength in the $n^{th}$ distance-based fluctuation data and based on the reflected waves from the detection part of the living body H2. The fluctuation data generation unit 45 may generate time-based fluctuation data in which the corresponding strength information are arranged in time series by performing the strength obtaining process associated with the living body H2 on the first to $N^{th}$ distance-based fluctuation data. For example, the fluctuation data generation unit 45 may obtain, as time-based fluctuation data, a group of signal strengths arranged in time series at the reference value in the corrected time-series data relating to the living body H2.

Figure 18A:
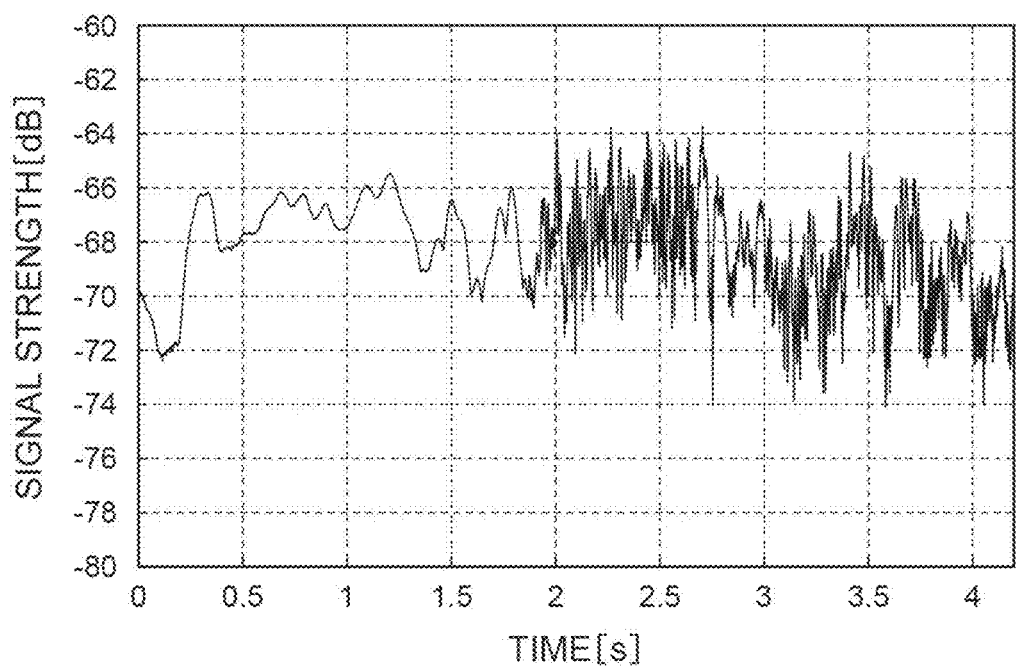
FIG. 18A is a graph showing a temporal change in signal strength obtained from time-series data that are not corrected.
Figure 18B:
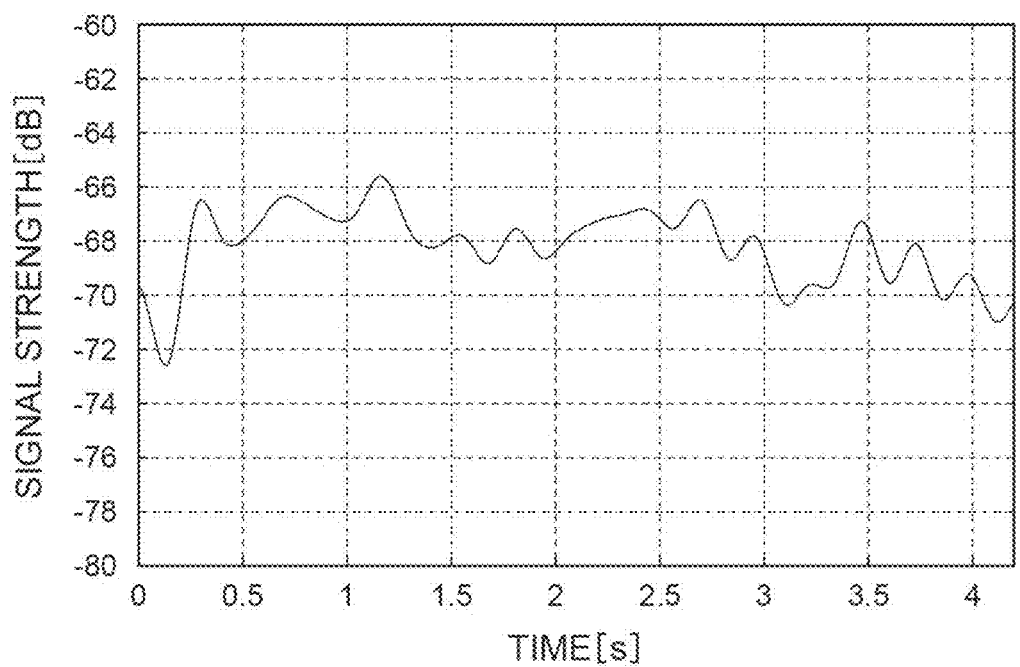
FIG. 18B is a graph showing a temporal change in signal strength obtained from corrected time-series data.

FIG. 18A shows temporal change in signal strength at a reference value (for example, the distance is 2.2 m) in the time-series data before correcting shown in FIG. 14. FIG. 18B shows temporal change in signal strength at the reference value in the corrected time-series data shown in FIG. 17. In the temporal change in signal strength shown in FIG. 18A, signal strengths of reflected waves from the reflection position other than the detection part of the living body H2 are obtained from about two seconds after the start of the measurement. In the temporal change in signal strength shown in FIG. 18B, since the time-series data is corrected, signal strengths of reflected waves from the detection part of the living body H2 are continuously obtained. Since the living body H2 gradually moves away from the transmitting and receiving device 10, signal strengths are generally reduced in the latter half.

The biological data generation unit 46 may generate the biological data of the detection part of the living body H1 based on the time-based fluctuation data relating to the living body H1, For example, the biological data generation unit 46 may generate the biological data of the detection part of the living body H1 by performing multiple resolution analysis on the time-based fluctuation data relating to the living body H1. The biological data generation unit 46 may generate the biological data of the detection part of the living body H2 based on the time-based fluctuation data relating to the living body H2. For example, the biological data generation unit 46 may generate the biological data of the detection part of the living body H2 by performing multiple resolution analysis on the time-based fluctuation data relating to the living body H2.

In the biological data obtaining device 20 of the example described above, even if a plurality of living bodies are present in the detection region R, it is possible to monitor biological data of each of the plurality of living bodies.

In some examples, when the living body H as a detection target is a human being, there is a case where the living body H moves while staying in the same place (for example, when working at a desk or driving a car). In this case, the time-series data obtained by the data obtaining unit 41 is close to the state shown in FIG. 6B. In such a case, the data correction unit 44 may perform the secondary correction and the tertiary correction without calculating the approximate line for each block (without performing the primary correction). When the movement is limited, the data correction unit 44 may increase the number of range bins included in the scattering range.

In some examples, the biological data generation unit 46 may calculate (generate) at least one of the average respiratory rate and the average heart rate as biological data by performing a Fast Fourier Transform (FFT) or wavelet transform on the time-based fluctuation data instead of the multiple resolution analysis described above. The pulsation signal is weaker than the respiration signal. However, for example, by setting the observation time as long as several minutes, it is possible to estimate the average respiratory rate and heart rate (respiratory spectrum and pulsation spectrum) of the moving living body H.

In some examples, after performing the secondary correction, the data correction unit 44 may calculate an error for each block based on the deviation between the distance component at the peak of the signal strength in the $n^{th}$ distance-based fluctuation data and the reference value in the block. The data correction unit 44 may determine whether or not the calculated error is smaller than a predetermined threshold value. The data correction unit 44 may repeatedly perform the generation process, the primary correction, and the secondary correction until the error becomes smaller than the predetermined threshold value. For example, the data correction unit 44 may calculate, as the above error, a root mean square error between the distance component at the peak in each of the pieces of first to $N^{th}$ distance-based fluctuation data and the reference value. The data correction unit 44 may perform the tertiary correction when the error for each block becomes smaller than the predetermined threshold value. The reference value may be, for example, the actual position of the living body H.

Figure 19:
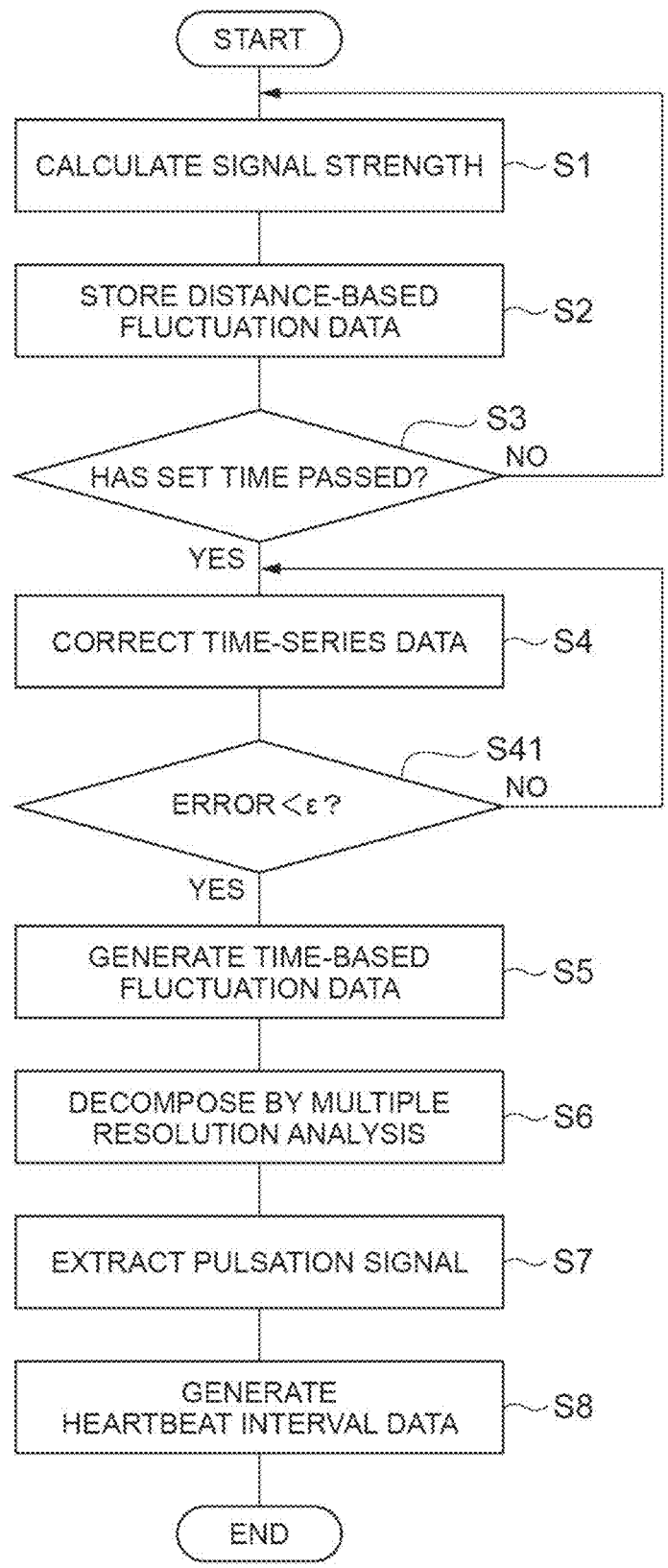
FIG. 19 is a flowchart for describing a procedure for obtaining biological data.

In some examples, the data correction unit 44 may perform the generation process, the primary correction, and the secondary correction without calculating an error and, after performing the tertiary correction, may calculate the error in the same manner as described above by using the reference value of one block (for example, the first block B1) as a reference. The biological data obtaining method shown in FIG. 19 is different from the obtaining method shown in FIG. 10 in that step S41 is further executed. After correcting the time-series data in step S4, the data correction unit 44 determines whether or not the error is smaller than a threshold value c (step S41). When it is determined in step S41 that the error is equal to or greater than the threshold value ε (step S41: NO), the data correction unit 44 executes the correction process of step S4 again. When it is determined in step S41 that the error is smaller than the threshold value s (step S41: YES), the control unit 24 executes a series of processes of steps S5 to S8.

Figure 20:
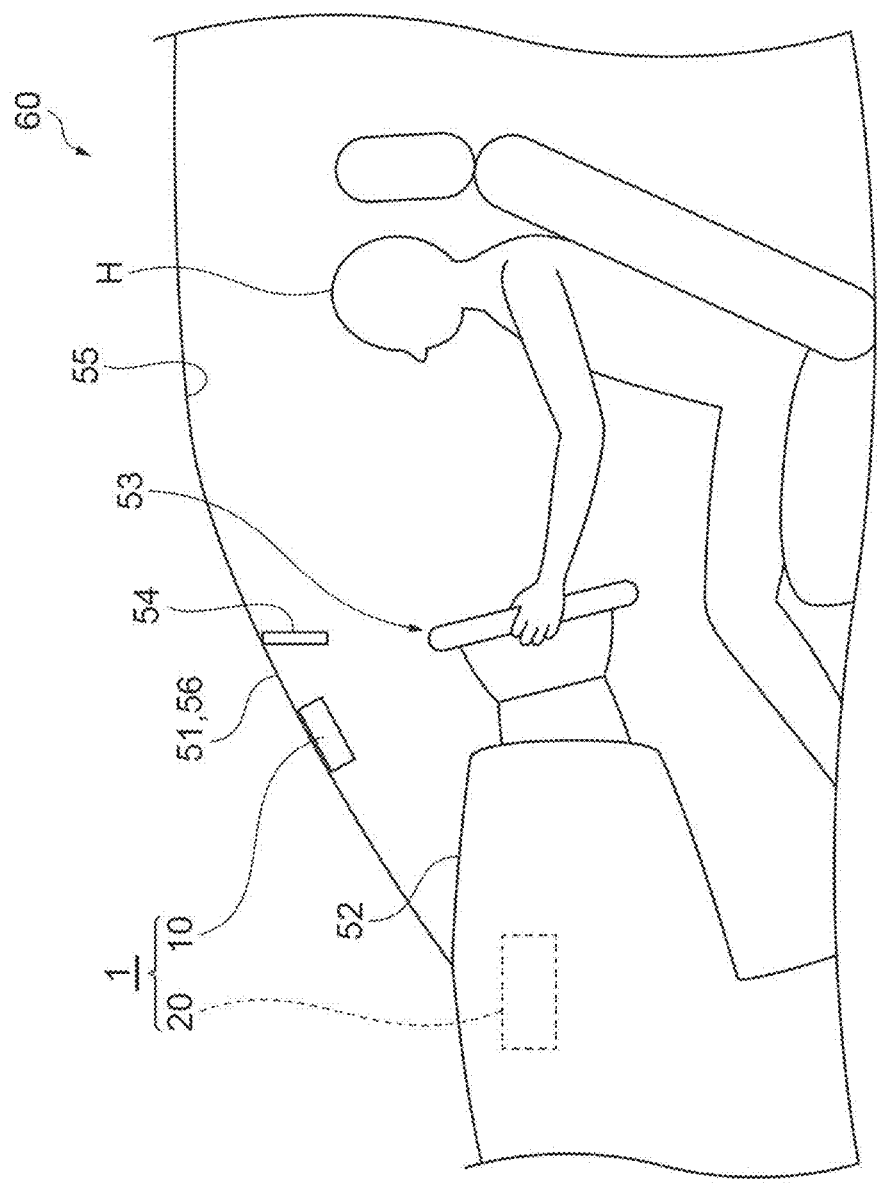
FIG. 20 is a schematic diagram schematically showing an example of a vehicle including a biological data obtaining system.

In some examples, the biological data Obtaining system 1 may be provided in a vehicle. The biological data obtaining system 1 may obtain biological data of the living body H, which is a detection target, present in a detection region R set in the vehicle. Examples of the vehicle include an automobile, a motorcycle, a railcar, a ship, an airplane, and a helicopter. Examples of the detection target in the vehicle include an operator (driver) and a passenger of the vehicle. FIG. 20 shows a vehicle 60 in which the biological data obtaining system 1 is provided.

As shown in FIG. 20, the biological data obtaining system 1 may be provided inside the vehicle 60. For example, the transmitting and receiving device 10 of the biological data obtaining system 1 may be disposed so that the detection region R includes the driver's seat of the vehicle 60. As an example, the transmitting and receiving device 10 may be provided on a windshield 51 as shown in FIG. 20. The transmitting and receiving device 10 may be provided at any of a dashboard 52, a steering wheel member 53, a rearview mirror 54, and a roof panel 55 instead of the windshield 51. Alternatively, the transmitting and receiving device 10 may be provided on a pillar 56 (A pillar located next to the windshield 51) closer to the driver's seat. The biological data obtaining device 20 of the biological data obtaining system 1 may also be disposed in the vehicle 60. The biological data obtaining device 20 (see FIG. 11) including the transmitter 11 and the receiver 12 may be disposed at any of the above locations.

When the biological data obtaining system 1 is provided in the vehicle 60, the biological data obtaining device 20 may execute a series of processes of the data obtaining method shown in FIG. 10 or 19. In this case, the first to $N^{th}$ distance-based fluctuation data obtained by repeatedly executing steps S1 to S3 is data based on radio waves reflected from the living body H in the vehicle 60. The time-based fluctuation data may be generated by executing the processes of steps S4 and S5 on the time-series data based on the reflected waves from the living body H in the vehicle 60.

The biological data generation unit 46 may generate a plurality of decomposed signals by performing eight wavelet transforms on the time-based fluctuation data unlike in the above example (seven wavelet transforms). For example, when extracting the pulsation signal, the biological data generation unit 46 may exclude a non-pulsation signal corresponding to the vibration applied to the living body H due to the vehicle 60 in addition to the respiration signal. The biological data generation unit 46 may exclude decomposed signals having a frequency range including the natural frequency of the vibration caused by the vehicle 60. The biological data generation unit 46 may extracts a pulsation signal corresponding to the pulsation of the living body H by recombining a plurality of remaining decomposed signals after excluding the respiration signal and the non-pulsation signal caused by the vehicle 60. The biological data generation unit 46 may generate biological data (for example, heartbeat interval data) by performing spectral analysis using an AR model on the pulsation signal in the same manner as described above.

Figure 21:
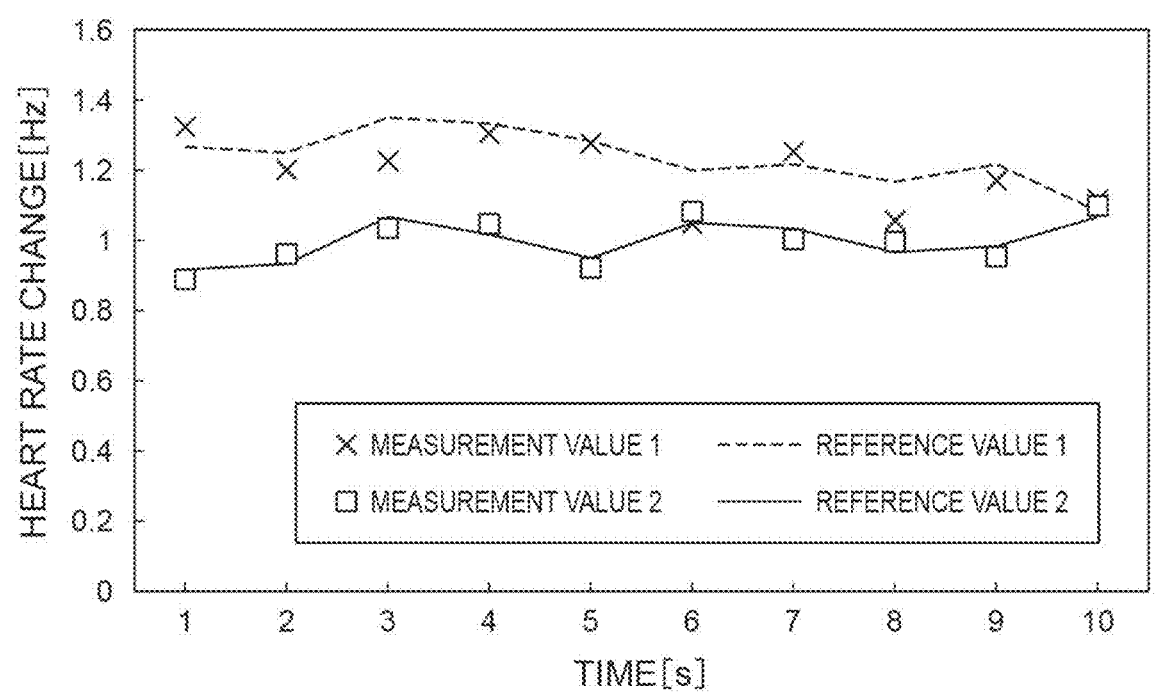
FIG. 21 is a graph showing an example of heartbeat interval data obtained from a living body in a vehicle.

FIG. 21 shows an example of heartbeat interval data obtained from the living body H in the vehicle 60. The heartbeat interval data shown in FIG. 21 is measurement results of the heart rate change (Hz) of a driver in the vehicle 60 (automobile) traveling on the road. In FIG. 21, two measurement results are shown. The heart rate change (Hz) corresponds to the reciprocal of the driver's heartbeat interval (s). In FIG. 21, the "measurement value 1" is a first measurement value obtained by performing seven wavelet transforms and excluding the respiration signal, and the "measurement value 2" is a second measurement value obtained by performing eight wavelet transforms and excluding the respiration signal and the non-pulsation signal caused by the vehicle 60. The "reference value 1" corresponds to the measurement value 1, and the "reference value 2" corresponds to the measurement value 2. The reference value 1 and the reference value 2 are measurement values obtained with a contact type sensor for comparison. The reference value 1 and the reference value 2 are measured by attaching a PPG (optical heart rate sensor) to a fingertip of the driver when obtaining the measurement value 1 and the measurement value 2. In addition, the transmitting and receiving device 10 is attached to the pillar 56 close to the driver's seat to measure biological data.

From the measurement result shown in FIG. 21, it can be seen that the heartbeat interval data of the living body H is obtained even in the vehicle 60 as in the result shown in FIG. 9. In addition, the correlation between the measurement value 1 and the reference value 1 is 0.95 or less, and the correlation between the measurement value 2 and the reference value 2 is 0.96 to 0.97. From this, it can be seen that the error included in the measurement value 2 is smaller than the error in the measurement value 1 assuming that the reference value measured in contact with the living body H is a true value. That is, by excluding the non-pulsation signal caused by the vehicle 60, the biological data of the living body H in the vehicle 60 is detected more accurately.

In the vehicle 60 including the biological data obtaining device 20 of the above example, it is possible to monitor the biological data of one or more living bodies in the vehicle 60. Since the biological data generation unit 46 generates pulsation data after excluding the non-pulsation signal caused by the vehicle 60, it is possible to accurately detect the pulsation data even if the information caused by the vehicle 60 is included in the time-series data. In addition, by performing the correction process described above, it is possible to accurately detect biological data even if there is a movement during driving by the driver. Some example of the movement during driving includes a movement for check in the left-right direction and movements associated with various operations.

Figure 22:
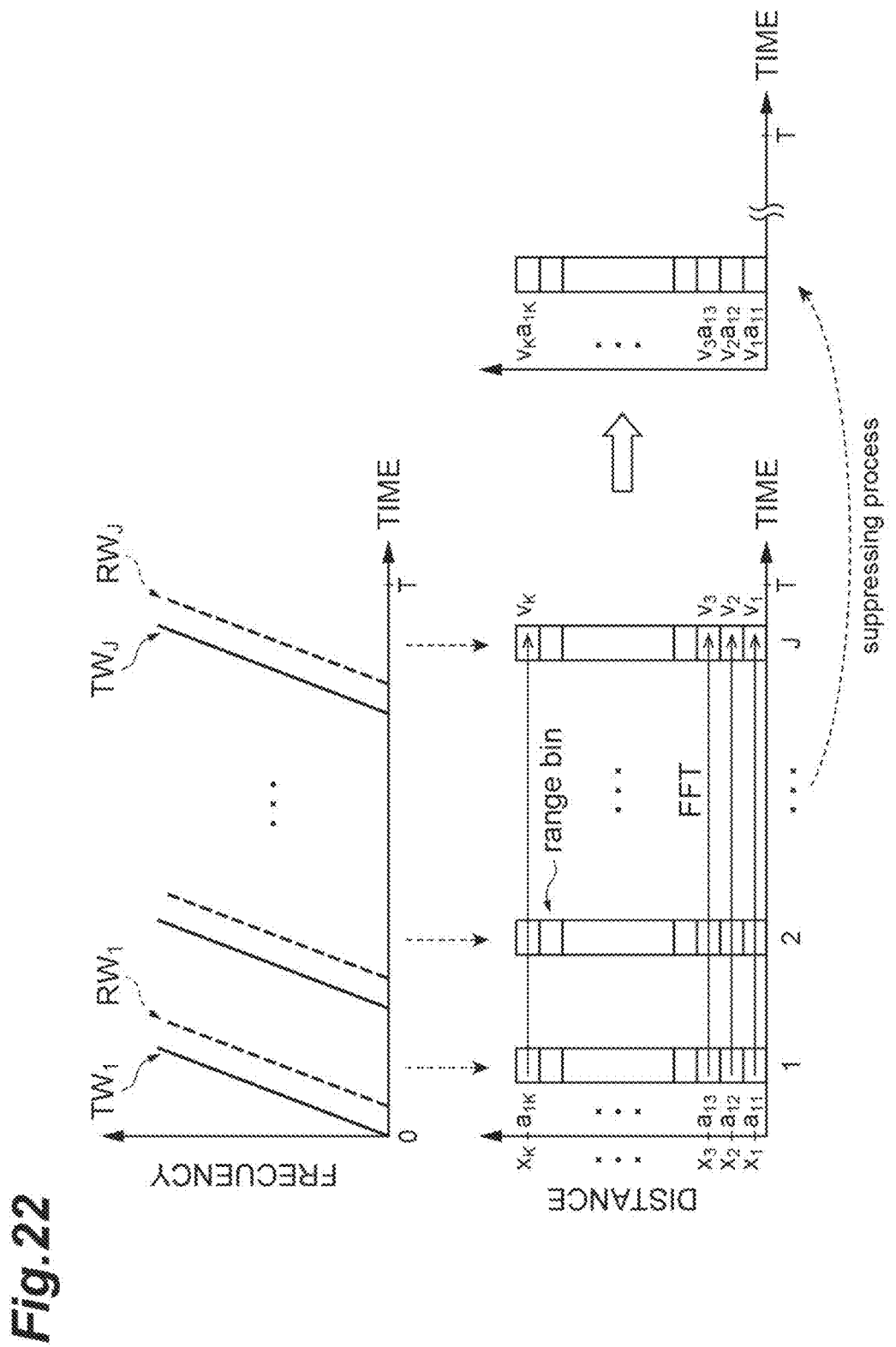
FIG. 22 is a schematic diagram for describing a procedure for calculating time-series data.

The biological data obtaining device 20 may generate the time-series data including the first to $N^{th}$ distance-based fluctuation data by performing a process for suppressing the influence of unnecessary reflected waves from an object other than the living body. Some examples of unnecessary reflected waves include walls and fixtures (for example, desks or chairs). Hereinafter, the process for reducing the influence of unnecessary reflected waves is referred to as "suppressing process". FIG. 22 is a schematic diagram for describing the suppressing process.

The transmitter 1 and the receiver 12 may constitute a frequency modulation (FM) radar. The transmitter 11 may be configured to sequentially transmit a plurality of transmission waves TW, which are the radio waves, toward the detection region R. The transmitter 11 may transmit each of the plurality of transmission waves TW at different timings arranged in time series order. The transmitter 11 may transmit each of the plurality of transmission waves TW at fixed time intervals. The transmitter 11 is configured to transmit, for example, 40 to 140 transmission waves TW in 0.1 seconds.

The receiver 12 is configured to receive a plurality of reception waves RW obtained by the plurality of transmission waves TW being reflected in the detection region R. The plurality of reception waves RW are reflected waves of the radio waves described above. As shown in FIG. 22, the transmitter 11 and the receiver 12 alternately repeat transmission of one transmission wave TW and reception of one reception wave RW The receiver 12 may extract a signal for each range bin included in first to $K^{th}$ range bins (the plurality of range bins) obtained by dividing the detection region R along the distance direction. K is a natural number of 2 or more, and indicates the number of the plurality of range bins. In FIG. 22, the distance (position) of each of the first to $K^{th}$ range bins are indicated by x1, x2, x3, . . . , xK.

In the suppressing process, $n^{th}$ distance-based fluctuation data is generated per an arbitrarily set frame period (for each frame period). A length T of one frame period may be about 0.01 to 0.2 seconds. When the length T of one frame period is set to 0.1 seconds, the n-th distance-based fluctuation data may be generated based on 40 to 140 reception waves RW corresponding to 40 to 140 transmission waves TW. In the example shown in FIG. 22, transmission waves $TW_1$, $TW_2$, . . . , $TW_J$ are transmitted and reception waves $RW_1$, $RW_2$, . . . , $RW_J$ are received in one frame period. J is a natural number of 2 or more, and for example, when the length T of the frame period is 0.1 seconds, J may be 40 to 140.

The signal strength calculation unit 42 may calculate a signal strength in each of the first to $K^{th}$ range bins based on reception data corresponding to one reception wave RW. The signal strength calculation unit 42 may generate (calculate) first to $J^{th}$ reception signal data based on reception data corresponding to a plurality of reception waves RW received in one frame period. The signal strength calculation unit 42 may generate $j^{th}$ reception signal data of the first to $J^{th}$ reception signal data based on reception data corresponding to reception wave RWj, where j is a natural number of 1 to J.

The first to $J^{th}$ reception signal data are obtained based on reflected waves which are reflected in the detection region R at different times arranged in time series order in one frame period, the reflected waves are wide band radio waves or ultra wide band radio waves. The $j^{th}$ reception signal data (each of the first to $J^{th}$ reception signal data) indicates changes in signal strength with respect to distance. The signal strength may be indicated by a complex number or an IQ signal (In-Phase/Quadrature-Phase signal). The $j^{th}$ reception signal data includes signal strengths $a_{j1}$ to $a_{jK}$ in the first to $K^{th}$ range bins. For example, "y" in signal strength $a_{yz}$ indicates that it is the signal strength of $y^{th}$ reception signal data, and "z" in signal strength $a_{yz}$ indicates that it is the signal strength in $z^{th}$ range bin, where y is a natural number of 1 to J, and z is a natural number of 1 to K. The signal strength of the $j^{th}$ reception signal data in a first range bin is represented by $a_{j1}$, and the signal strength of the $j^{th}$ reception signal data in a second range bin is represented by $a_{j2}$. The signal strengths of the $j^{th}$ reception signal data in third to $(K-1)^{th}$ range bins are respectively represented by $a_{j3}$ to $a_{j(K-1)}$. The signal strength of the $j^{th}$ reception signal data in the $K^{th}$ range bin is represented by $a_{jK}$.

First reception signal data includes signal strengths $a_{11}$, $a_{12}$, . . . , $a_{1K}$ in the first to $K^{th}$ range bins. Second reception signal data includes signal strengths $a_{21}$, $a_{22}$, . . . , $a_{2K}$ in the first to $K^{th}$ range bins. $J^{th}$ reception signal data includes signal strengths $a_{J1}$, $a_{J2}$, . . . , $a_{JK}$ in the first to $K^{th}$ range bins. The storage unit 43 may store the first to $J^{th}$ reception signal data generated by the signal strength calculation unit 42. The signal strength calculation unit 42 may generate the $n^{th}$ distance-based fluctuation data by performing the suppressing process on the first to $J^{th}$ reception signal data.

The suppressing process may include coefficient calculation process and data generation process. The signal strength calculation unit 42 may perform, as the coefficient calculation process, a process of calculating a coefficient $v_i$ based on the result obtained by frequency-converting signal strengths $a_{1i}$ to $a_{Ji}$, where i is a natural number of 1 to K. The signal strength calculation unit 42 may frequency-convert time data including signal strengths $a_{1i}$ to $a_{Ji}$. When performing the coefficient calculation process, the signal strength calculation unit 42 may, for each range bin included in the first to $K^{th}$ range bins, apply frequency conversion to the time data including a plurality of signal strengths of the first to $J^{th}$ reception signal data in each range bin. The signal strength calculation unit 42 may calculate the coefficient $v_i$ based on a result obtained by frequency-converting the signal strengths $a_{1i}$ to $a_{ji}$ for all of the first to $K^{th}$ range bins.

The signal strength calculation unit 42 may calculate a coefficient $v_1$ based on the result obtained by frequency-converting time data including signal strengths $a_{11}$ to $a_{j1}$ in a first range bin. The signal strength calculation unit 42 may calculate a coefficient $v_2$ based on the result obtained by frequency-converting time data including signal strengths $a_{12}$ to $a_{j2}$ in a second range bin. The signal strength calculation unit 42 may calculate coefficients $v_3$ to $v_K$ in third to $K^{th}$ range bins in a manner similar to that of the first range bin. The signal strength calculation unit 42 may calculate a coefficient based on the result obtained by frequency conversion for each of the range bins. The time data includes a time axis and a signal strength axis, and indicates temporal changes in signal strength in one range bin.

The signal strength calculation unit 42 may frequency-convert the signal strengths $a_{1i}$ to $a_{ji}$ using a Fast Fourier Transform. The signal strength calculation unit 42 may extract the frequency of a frequency component having the largest value in a frequency spectrum obtained by the frequency conversion of the plurality of signal strengths for each of the range bins. The signal strength calculation unit 42 may calculate the coefficient by normalizing a plurality of frequencies extracted in each of the first to $K^{th}$ range bins. The signal strength calculation unit 42 may perform normalization so that the largest frequency of the plurality of frequencies is 1.

The signal strength calculation unit 42 may perform, as the data generation process, a process of calculating the $n^{th}$ distance-based fluctuation data by multiplying a plurality of signal strengths in any one of the first to $J^{th}$ reception signal data by the coefficient $v_i$. The signal strength calculation unit 42 may calculate the $n^{th}$ distance-based fluctuation data by multiplying the signal strength $a_{ji}$ by the coefficient $v_i$ in each of the first to $K^{th}$ range bins for the $j^{th}$ reception signal data. The signal strength of the $n^{th}$ distance-based fluctuation data in the first range bin is obtained by multiplying signal strength $a_{j1}$ by the coefficient $v_1$. The signal strength of the $n^{th}$ distance-based fluctuation data in the second range bin is obtained by multiplying signal strength $aj_2$ by the coefficient $v_2$. The signal strengths of the $n^{th}$ distance-based fluctuation data in the third to $(K-1)^{th}$ range bins are respectively obtained by multiplying signal strengths $aj_3$ to $aj_{(K-1)}$ by the coefficient $v_3$ to $v_{(K-1)}$. The signal strength of the $n^{th}$ distance-based fluctuation data in the $K^{th}$ range bin is obtained by multiplying signal strength $aj_K$ by the coefficient $v_K$. The signal strength calculation unit 42 may calculate the $n^{th}$ distance-based fluctuation data by multiplying the signal strength $a_{ji}$ by the coefficient $v_i$ in each of the first to $K^{th}$ range bins for the first reception signal data.

Figure 23:
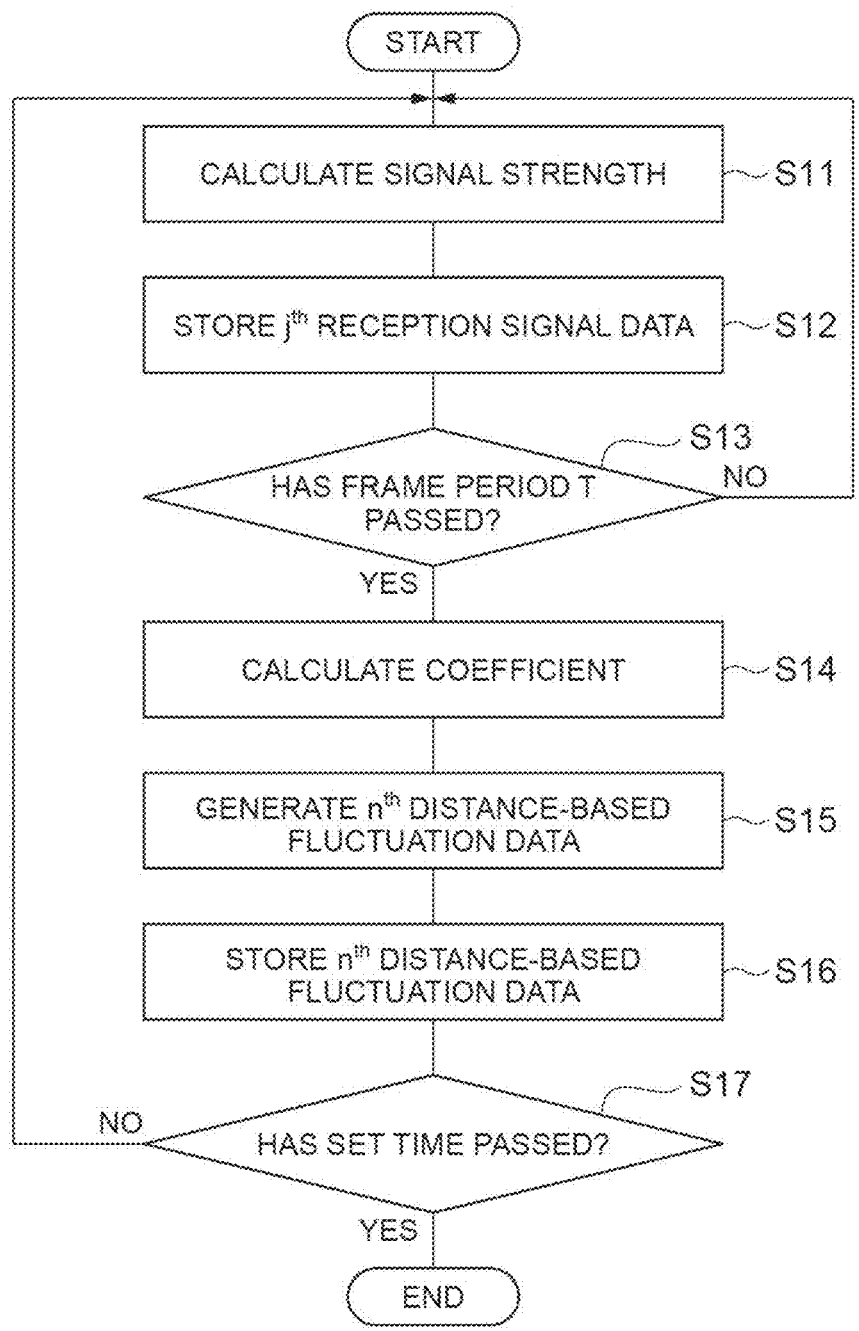
FIG. 23 is a flowchart for describing a procedure for calculating time-series data.

The signal strength calculation unit 42 may calculate $(n+1)^{th}$ distance-based fluctuation data by calculating the $n^{th}$ distance-based fluctuation data in one frame period and then performing the suppressing process on first to $J^{th}$ reception signal data obtained in the next frame period. FIG. 23 is a flowchart showing an example of a procedure for generating time-series data including the first to $N^{th}$ distance-based fluctuation data. First, the signal strength calculation unit 42 calculates signal strengths $a_{11}$ to $a_{1K}$ in the first to $K^{th}$ range bins, respectively, based on reception data corresponding to reception wave $RW_1$ to obtain first reception signal data indicating changes in signal strength with respect to distance (step S11 in FIG. 23).

Next, the storage unit 43 stores the first reception signal data obtained in step S11 (step S12 in FIG. 23). Then, the control unit 24 determines whether or not one frame period has passed from a start time of the first step S11 (step S13 in FIG. 23). When it is determined that one frame period has not passed (step S13: NO), the control unit 24 repeats steps S11 to S13. In the second step S11, the signal strength calculation unit 42 generates second reception signal data, and in the $J^{th}$ step S11, the signal strength calculation unit 42 generates $J^{th}$ reception signal data. As a result, a data group including the first to $J^{th}$ reception signal data is stored in the storage unit 43 in one frame period.

When it is determined that one frame period has passed (step S13: YES), the signal strength calculation unit 42 calculates coefficients $v_1$ to $v_K$ in the first to $K^{th}$ range bins (step S14 in FIG. 23). The signal strength calculation unit 42 may calculate the coefficient $v_i$ based on the result obtained by frequency-converting time data including signal strengths $a_{1i}$ to $a_{ji}$ in each of all of the first to $K^{th}$ range bins. The signal strength calculation unit 42 then may multiply signal strength $a_{1i}$ of the first reception signal data in each of the first to $K^{th}$ range bins by the coefficient $v_i$ to generate first distance-based fluctuation data (step S15 in FIG. 23).

Next, the storage unit 43 stores the first distance based fluctuation data generated in step S15. Then, the control unit 24 determines whether or not the set time has passed from an initial time (step S17 in FIG. 23). When it is determined that the set time has not passed (step S17: NO), the process performed by the control unit 24 returns to step S11. Thereafter, a series of processes including the repeating process of steps S11 to S13 and steps S14 to S17 is repeated to generate and store second to $N^{th}$ distance-based fluctuation data.

When it is determined that the set time has passed (step S17: YES), the process of obtaining the time series data in one set time ends. The control unit 24 may then perform a series of processes of steps S4 to S8 shown in FIG. 10 to generate biological data such as heartbeat interval data based on the time series data obtained after being subjected to the suppressing process.

In the suppressing process, coefficients are calculated based on the result obtained by frequency-converting a plurality of signal strengths arranged in time series in one range bin. In one range bin in which a wall or the like other than a living body, which is an object to be detected, is present, since the temporal change of the plurality of signal strengths is small, a low frequency component is obtained by frequency-convening the plurality of signal strengths arranged in time series in the one range bin. In another range bin in which a moving living body is present, the temporal change of a plurality of signal strengths is relatively large due to the action (movement) of the living body, and a high frequency component is obtained by frequency-convening the plurality of signal strengths arranged in time series in the another range bin. Thus, the coefficient in the range bin in which an object other than an object to be detected is present can be small, and the coefficient in the range bin in which a living body is present can be large. As a result, in the $n^{th}$ distance-based fluctuation data, the difference between the signal strength based on reflected waves from the object other than the object to be detected and the signal strength based on reflected waves from the living body can be increased. The biological data can thus be detected more accurately.

The time series data shown in FIG. 24A include a plurality of distance-based fluctuation data obtained in about 60 seconds, and are obtained by performing integration process described later instead of the suppressing process. The time series data shown in FIG. 24B include a plurality of distance-based fluctuation data obtained in about 60 seconds, and are obtained by performing the suppressing process. The time series data shown in FIG. 24A and the time series data shown in FIG. 24B are different in the methods for calculating the distance-based fluctuation data, but the plurality of distance-based fluctuation data are calculated based on the same reception data.

The reception data are obtained in a measurement environment in which the living bodies H1 and H2, who are subjects, are walking in the detection region R. In the measurement environment, the living body H1 walks so as to reciprocate between a location about 1.2 m away from the transmitting and receiving device 10 and a location about 4.5 m away from the transmitting and receiving device 10. In the measurement environment, the living body H2 walks so as to reciprocate between a location about 4.0 in away from the transmitting and receiving device 10 and a location about 5.3 m away from the transmitting and receiving device 10. In the integration process, the $n^{th}$ distance-based fluctuation data are generated, for each range bin, based on an integrated value obtained by integrating time data including a plurality of signal strengths of the first to $J^{th}$ reception signal data in each range bin.

Figure 24A:
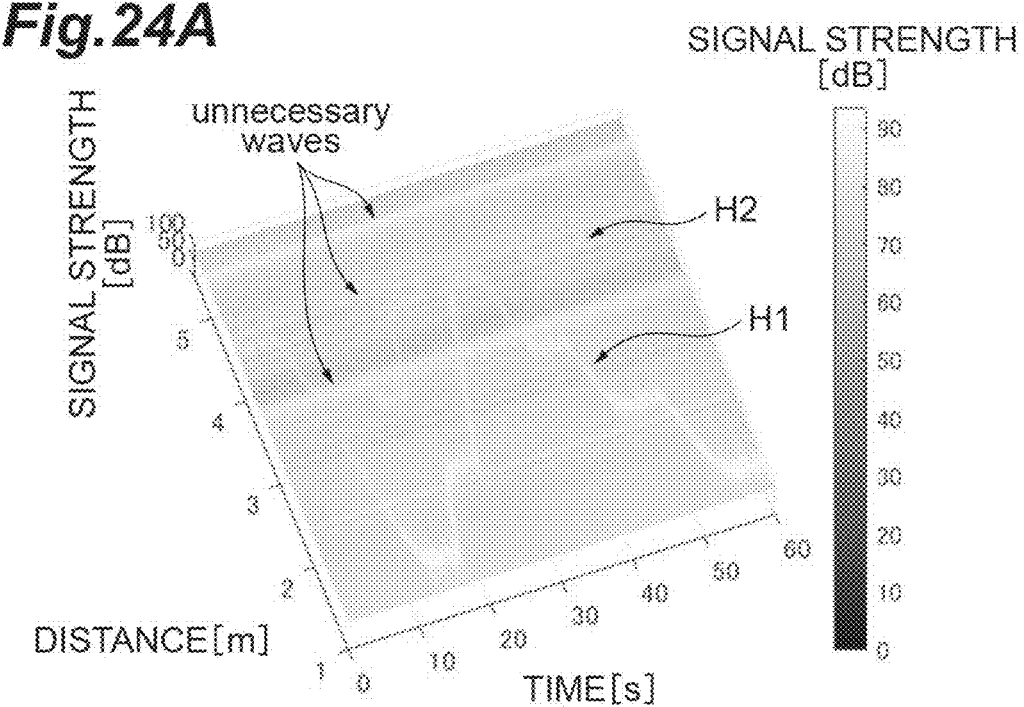
FIG. 24A is a graph showing an example of time-series data when suppressing process is not performed.
Figure 24B:
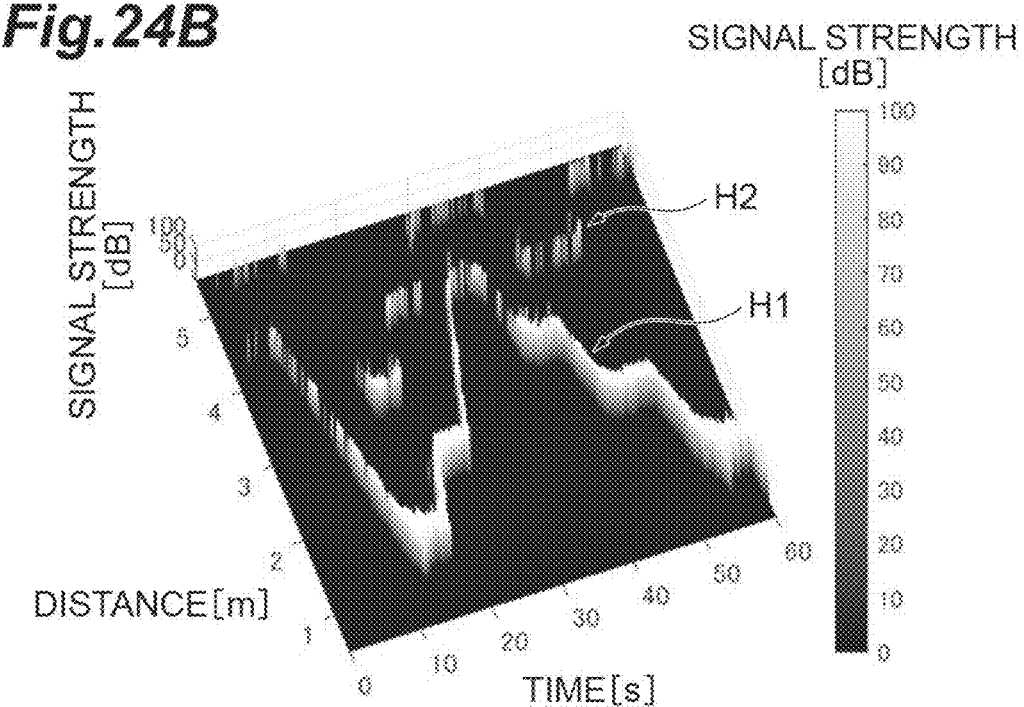
FIG. 24B is a graph showing an example of time-series data when suppressing process is performed.

The time series data shown in FIG. 24A includes signals based on unnecessary reflected waves from a location about 3.8 m away from the transmitting and receiving device 10, a location about 4.7 in away from the transmitting and receiving device 10, and a location about 5.4 m away from the transmitting and receiving device 10. In the time series data shown in FIG. 24A, the difference between the signal strength based on the reflected waves from the object other than the object to be detected and the signal strength based on the reflected waves from the living body H1 or the living body H2 is small. In the time series data shown in FIG. 24B, the strength of the signal based on the unnecessary reflected waves is almost zero. Thus, the difference between the signal strength based on the reflected waves from the object other than the object to be detected and the signal strength based on the reflected waves from the living body H1 or the living body H2 is large.

Even when the living body H1 or the living body H2 is stationary for at least a part of the period, since the movement of the living body includes movements made unconsciously, the temporal change in the plurality of signal strengths based on the living body may be larger than the temporal change in the plurality of signal strengths based on a fixed object. It is thus considered that the difference between the signal strength based on the reflected waves from the object other than the object to be detected and the signal strength based on the reflected waves from the living body H1 or the living body H2 is large due to the suppressing process being performed, similarly to the case in which intentional movements such as walking are made.

By performing the integration process, a portion of the noise component is reduced. The signal strength calculation unit 42 may perform an integration process in addition to the coefficient calculation process and the data generation process when executing the suppressing process. The signal strength calculation unit 42 may generate integrated signal data by integrating a plurality of reception signal data of the first to $J^{th}$ reception signal data, the integrated signal data include signal strengths $b_1$ to $b_K$ in the first to $K^{th}$ range bins. The signal strength of the integrated signal data in a first range bin is represented by $b_1$, and the integrated signal data in a second range bin is represented by $b_2$. The signal strengths of the integrated signal data in third to $(K-1)^{th}$ range bins are respectively represented by $b_3$ to $b_{(K-1)}$. The signal strength of the integrated signal data in the $K^{th}$ range bin is represented by $b_K$.

The signal strength calculation unit 42 may generate the integrated signal data by integrating first to $r^{th}$ reception signal data of the first to $J^{th}$ reception signal data, r is a natural number of 2 or more, and r may be smaller than J. The signal strength calculation unit 42 may calculate the signal strengths $b_1$ to $b_K$, for each range bin, based on an integrated value obtained by integrating a plurality of signal strengths of the first to $r^{th}$ reception signal data in each range bin. The signal strength calculation unit 42 may calculate the signal strength $b_i$ based on an integrated value obtained by integrating the signal strengths $a_{1i}$ to $a_{ri}$ for all of the first to $K^{th}$ range bins. The signal strength calculating unit 42 may calculate the integrated value, as the signal strength $b_i$, obtained by integrating the signal strengths $a_{1i}$ to $a_{ri}$. The signal strength calculating unit 42 may calculate a value, as the signal strength $b_i$, obtained by arithmetically averaging the integrated value obtained by integrating the signal strength $a_{1i}$ to $a_{ri}$.

The signal strength calculation unit 42 may calculate the signal strength $b_1$ based on an integrated value obtained by integrating the signal strengths $a_{11}$ to $a_{r1}$ in the first range bin. The signal strength calculation unit 42 may calculate the signal strength $b_2$ based on an integrated value obtained by integrating the signal strengths $a_{12}$ to $a_{r2}$ in the second range bin. The signal strength calculation unit 42 may respectively calculate the signal strengths $b_3$ to $b_{(K-1)}$ in a manner similar to that of the first range bin. The signal strength calculation unit 42 may calculate the signal strength $b_K$ based on an integrated value obtained by integrating the signal strengths $a_{1K}$ to $a_{rK}$ in the $K^{th}$ range bin.

The signal strength calculation unit 42 may calculating the $n^{th}$ distance-based fluctuation data by multiplying the signal strength $b_i$ by the coefficient $v_i$ in each of the first to $K^{th}$ range bins for the integrated signal data when executing the data generation process. The signal strength of the $n^{th}$ distance-based fluctuation data in the first range bin may be obtained by multiplying signal strength $b_1$ by the coefficient $v_1$. The signal strength of the $n^{th}$ distance-based fluctuation data in the second range bin may be obtained by multiplying signal strength $b_2$ by the coefficient $v_2$. The signal strengths of the $n^{th}$ distance-based fluctuation data in the third to $(K-1)^{th}$ range bins may be respectively obtained by multiplying signal strengths $b_3$ to $b_{(K-1)}$ n by the coefficients $v_3$ to $v_{(K-1)}$. The signal strength of the $n^{th}$ distance-based fluctuation data in the $K^{th}$ range bin may be obtained by multiplying signal strength $b_K$ by the coefficient $v_K$.

In the example above, after the SN ratio of a portion of the reception signal data is improved by the integration process, the multiplication of the coefficients $v_1$ to $v_K$ is performed. In the n-th distance-based fluctuation data, the difference between the signal strength based on the reflected waves from the object other than the object to be detected and the signal strength based on the reflected waves from the living body H1 or the living body H2 can be increased. The biological data can thus be detected more accurately.

When the detection region R is set indoors, the movement of the living body in one frame period can be ignored in many cases. However, when the movement of the living body H is faster and the movement of the living body cannot be ignored in one frame period, the detection accuracy of the living body data may be reduced. The signal strength calculation unit 42 may perform frame set process before performing the suppressing process. The frame set process may include obtaining movement information indicating a speed of movement of the living body H, and setting the length of the frame period based on the speed indicated by the movement information.

The signal strength calculation unit 42 may obtain the movement information obtained from a device other than the biological data obtaining device 20, the movement information may be obtained by that device. The biological data obtaining device 20 may calculate the movement information. When the speed of movement of the living body H is equal to or less than a predetermined threshold value, the signal strength calculation unit 42 may set the length of the frame period to a standard value (for example, 0.1 seconds). When the speed of movement of the living body H is greater than the threshold value, the signal strength calculation unit 42 may set the length of the frame period to a value smaller than a standard value (for example, 0.01 seconds). The signal strength calculation unit 42 may change the amount of adjustment of the length of the frame period in accordance with the difference between the speed of movement of the living body H and the threshold value, in the example above, when the motion of the living body H becomes faster, the frame period can be shortened. When the frame period is short, it is easy to reflect the movement of the living body in the first to $N^{th}$ distance-based fluctuation data. The biological data can thus be detected more accurately.

An example biological data obtaining device includes a storage unit, a first generation unit, and a second generation unit. The storage unit is configured to store time-series data in which first to $N^{th}$ distance-based fluctuation data are arranged in time series order. The first to $N^{th}$ distance-based fluctuation data are obtained based on reflected waves which are reflected from a living body at different times arranged in time series order, wherein the reflected waves are wide band radio waves or ultra wide band radio waves, $n^{th}$ distance-based fluctuation data of the first to $N^{th}$ distance-based fluctuation data indicates changes in signal strength with respect to distance. N is a natural number of 2 or more, and n is a natural number of 1 to N. The first generation unit is configured to generate time-based fluctuation data in which a plurality of corresponding strength information are arranged in time series by performing strength obtaining process on the first to $N^{th}$ distance-based fluctuation data. The strength obtaining process includes obtaining one corresponding strength information of the plurality of corresponding strength information, the one corresponding strength information is a signal strength included in the $n^{th}$ distance-based fluctuation data and based on reflected waves from a predetermined detection part of the living body. The second generation unit is configured to generate biological data of the detection part of the living body based on the time-based fluctuation data. In this case, the distance-based fluctuation data which are a number of data sets obtained from the reflected waves in a predetermined period are stored in the storage unit as time-series data. Then, from the time-series data, time-based fluctuation data in which signal strengths based on the reflected waves from the detection part are arranged in time series can be obtained. Since the signal strengths included in the time-based fluctuation data are based on the reflected waves from the detection part of the living body, even if the living body that is a detection target moves, the biological data can be Obtained based on the signal strengths based on the reflected waves form the detection part. As a result, it is possible to accurately detect biological data in a non-contact manner.

An example biological data obtaining device may further include a correction unit. The correction unit may be configured to obtain corrected time-series data by performing correction process on the first to $N^{th}$ distance-based fluctuation data. The correction process may include correcting distance components of the $n^{th}$ distance-based fluctuation data so that a distance component corresponding to the detection part of the living body in the $n^{th}$ distance-based fluctuation data approaches an arbitrary reference value. The first generation unit may be configured to obtain signal strengths at the arbitrary reference value from the corrected time-series data as the plurality of corresponding strength information, when performing the strength obtaining process. In this case, since distance components corresponding to the detection part is corrected so as to approach the reference value, the movement of the living body H is corrected in time-series data. Therefore, time-based fluctuation data of signal strength in which the influence of the movement of the living body is reduced is obtained, and the biological data is obtained based on the time-based fluctuation data. As a result, even if the living body H moves, it is possible to accurately detect the biological data of the living body.

In some examples, the correction process may include correcting distance components of $p^{th}$ to $q^{th}$ distance-based fluctuation data so that an approximate line approaches the arbitrary reference value, the $p^{th}$ to $q^{th}$ distance-based fluctuation data are included in the first to $N^{th}$ distance-based fluctuation data within a predetermined time. The approximate line may be obtained based on distance components of signal strength at a peak of the $p^{th}$ to $q^{th}$ distance-based fluctuation data, p and q are natural numbers satisfying $1 \leq p < q \leq N$. The movement line trajectory of the living body can be expressed by an approximate line of the distance component at a peak in the distance-based fluctuation data. Therefore, even if the distance-based fluctuation data includes a peak due to disturbance such as multipath, the peak can be excluded because the peak is far from the approximate line. For this reason, it is possible to more reliably detect biological data with high accuracy.

In some examples, the correction process may include performing block correction process on first to $M^{th}$ blocks that are obtained by sequentially dividing the time-series data in time series order. The block correction process may include correcting distance components of a plurality of distance-based fluctuation data of the first to $N^{th}$ distance-based fluctuation data so that an approximate line approaches an arbitrary block reference value, the plurality of distance-based fluctuation data are included in the $m^{th}$ block of the first to $M^{th}$ block. The approximate line may be obtained based on distance components of signal strength at a peak of the plurality of distance-based fluctuation data, the block reference value may be set for each of first to $M^{th}$ blocks. M is a natural number of 2 or more, and in is a natural number of 1 to M. In this case, since the approximate line showing the movement line trajectory of the living body H is calculated for each block, the approximate line can be made closer to the movement line trajectory of the living body H. Therefore, it is possible to detect biological data more accurately.

In some examples, the second generation unit may be configured to generate the biological data of the detection part of the living body by performing multiple resolution analysis on the time-based fluctuation data. Therefore, even if components other than the biological data are included in the time-based fluctuation data, the biological data can be obtained.

In some examples, the second generation unit may be configured to decompose the time-based fluctuation data into a plurality of decomposed signals by performing the multiple resolution analysis on the time-based fluctuation data. The second generation unit may be configured to generate pulsation data relating to pulsation of the living body based on a pulsation signal of the plurality of decomposed signals, the pulsation signal corresponds to the pulsation of the living body. In this case, the signal in the frequency range corresponding to the pulsation is extracted from the time-based fluctuation data by the multiple resolution analysis. Therefore, even if components other than the pulsation of the living body are included in the time-based fluctuation data, the pulsation data can be obtained.

In some examples, the second generation unit may be configured to generate heartbeat interval data indicating temporal change in heartbeat interval of the living body by spectrally analyzing the pulsation signal using an AR model. In this case, since noise included in the pulsation signal is removed by performing the spectral analysis using the AR model on the pulsation signal, it is possible to accurately detect the heartbeat interval.

In some examples, the first to $N^{th}$ distance-based fluctuation data may be obtained by oversampling the reflected waves based on a reference frequency corresponding to the pulsation of the living body. In this case, since the sampling period becomes short and accordingly more data can be obtained, it is easy to extract the pulsation signal from the time-based fluctuation data.

In some examples, the second generation unit may be configured to generate the pulsation data after excluding an extra signal of the plurality of decomposed signals, the extra signal corresponds to movement of the living body different from the pulsation. In this case, since the information due to the movement of the living body different from the pulsation are excluded from the time-based fluctuation data, it is possible to accurately detect the pulsation data.

In some examples, the first to $N^{th}$ distance-based fluctuation data may be obtained based on reflected waves which are reflected from the living body and another living body. The first generation unit may be configured to generate the time-based fluctuation data in which the plurality of corresponding strength information are arranged in time series order by performing the strength obtaining process on the first to $N^{th}$ distance-based fluctuation data. The strength obtaining process may include obtaining the one corresponding strength information of the plurality of corresponding strength information, the one corresponding strength information is a signal strength included in the $n^{th}$ distance-based fluctuation data and based on reflected waves from the predetermined detection part of the living body. The first generation unit may be configured to generate another time-based fluctuation data in which another plurality of corresponding strength information are arranged in time series order by performing the strength obtaining process on the first to $N^{th}$ distance-based fluctuation data. The strength obtaining process may include obtaining another one corresponding strength information of the another plurality of corresponding strength information, the another one corresponding strength information is a signal strength included in the $n^{th}$ distance-based fluctuation data and based on reflected waves from a predetermined detection part of the another living body. The second generation unit may be configured to generate the biological data of the detection part of the living body based on the time-based fluctuation data and to generate another biological data of the detection part of the another living body based on the another time-based fluctuation data. In this case, even if a plurality of living bodies are present in the detection region, it is possible to monitor biological data of each of the plurality of living body.

An example biological data obtaining device may further include a transmitting unit and a receiving unit. The transmitting unit may be configured to transmit the wide band radio waves or the ultra wide band radio waves. The receiving unit may be configured to receive the reflected waves. In this case, not a device separate from the biological data obtaining device but the biological data obtaining device itself has a function of transmitting and receiving radio waves. Therefore, the system can be simplified.

An example biological data obtaining device may further include a signal strength calculation unit configured to generate the $n^{th}$ distance-based fluctuation data by performing suppressing process on first to $J^{th}$ reception signal data. The first to $J^{th}$ reception signal data may be obtained based on reflected waves which are reflected in a detection region in which the living body is present at different times arranged in time series order in a frame period. The reflected waves may be the wide band radio waves or the ultra wide band radio waves, $j^{th}$ reception signal data of the first to $J^{th}$ reception signal data may indicate changes in signal strength with respect to distance. The $j^{th}$ reception signal data may include signal strengths $a_{j1}$ to $a_{jK}$ in first to $K^{th}$ range bins obtained by dividing the detection region in a distance direction, and J is a natural number of 2 or more, j is a natural number of 1 to J, and K is a natural number of 2 or more. The suppressing process may include calculating a coefficient $v_i$ based on a result obtained by frequency-converting the signal strengths $a_{1i}$ to $a_{ji}$ for all of the first to $K^{th}$ range bins, i is a natural number of 1 to K. The suppressing process may further include calculating the $n^{th}$ distance-based fluctuation data by multiplying the signal strength $a_{ji}$ by the coefficient v in each of the first to $K^{th}$ range bins for the $j^{th}$ reception signal data. In this case, in the $n^{th}$ distance-based fluctuation data, the difference between the signal strength based on reflected waves from the object other than the object to be detected and the signal strength based on reflected waves from the living body can be increased. The biological data can thus be detected more accurately.

In some examples, the suppressing process may includes calculating a coefficient $v_i$ based on a result obtained by frequency-converting the signal strengths $a_{1i}$ to $a_{ji}$ for all of the first to $K^{th}$ range bins, wherein i is a natural number of 1 to K. The suppressing process may further include generating integrated signal data by integrating a plurality of reception signal data of the first to $J^{th}$ reception signal data, wherein the integrated signal data include signal strengths $b_1$ to $b_K$ in the first to $K^{th}$ range bins. The suppressing process may further include calculating the $n^{th}$ distance-based fluctuation data by multiplying the signal strength $b_i$ by the coefficient $v_i$ in each of the first to $K^{th}$ range bins for the integrated signal data. In this case, in the n-th distance-based fluctuation data, the difference between the signal strength based on the reflected waves from the object other than the object to be detected and the signal strength based on the reflected waves from the object to be detected can be more increased. The biological data can thus be detected more accurately.

In some examples, the signal strength calculation unit may perform frame set process before performing the suppressing process. The frame set process may include obtaining movement information indicating a speed of movement of the living body and setting a length of the frame period based on the speed indicated by the movement information.

In this case, when the motion of the living body H becomes faster, the frame period can be shortened. When the frame period is short, it is easy to reflect the movement of the living body in the first to $N^{th}$ distance based fluctuation data. The biological data can thus be detected more accurately.

An example biological data obtaining system may include the biological data obtaining device, a transmitting unit, and a receiving unit. The transmitting unit may be configured to transmit the wide band radio waves or the ultra wide band radio waves. The receiving unit may be configured to receive the reflected waves. In this case, the same effect as in the above mentioned example is obtained.

An example biological data obtaining system may further include a communication unit configured to transmit reception data in accordance with the reflected wave to the biological data obtaining device with wireless communication. Capacity of the control unit (memory) that can be mounted in a device that performs at least one of radio wave transmission and reflected wave reception may be small, but a large amount of data can be handled by performing data storage and processing in a separate biological data Obtaining device. Therefore, it is possible to continue the detection of biological data for a long time.

An example vehicle includes a biological data obtaining device. The biological data obtaining device includes a storage unit, a first generation unit, and a second generation unit. The storage unit is configured to store time-series data in which first to $N^{th}$ distance-based fluctuation data are arranged in time series order. The first to $N^{th}$ distance-based fluctuation data are obtained based on reflected waves which are reflected from a living body at different times arranged in time series order, wherein the reflected waves are wide hand radio waves or ultra wide band radio waves, $n^{th}$ distance-based fluctuation data of the first to $N^{th}$ distance-based fluctuation data indicates changes in signal strength with respect to distance. N is a natural number of 2 or more, and n is a natural number of 1 to N. The first generation unit is configured to generate time-based fluctuation data in which a plurality of corresponding strength information are arranged in time series by performing strength obtaining process on the first to $N^{th}$ distance-based fluctuation data. The strength obtaining process includes obtaining one corresponding strength information of the plurality of corresponding strength information, the one corresponding strength information is a signal strength included in the $n^{th}$ distance-based fluctuation data and based on reflected waves from a predetermined detection part of the living body. The second generation unit is configured to generate biological data of the detection part of the living body based on the time-based fluctuation data. In this case, the same effect as in the above mentioned biological data obtaining device is obtained.

In some examples, the second generation unit may be configured to decompose the time-based fluctuation data into a plurality of decomposed signals by performing multiple resolution analysis on the time-based fluctuation data. The second generation unit may be configured to generate pulsation data relating to pulsation of the living body based on a pulsation signal of the plurality of decomposed signals after excluding an extra signal of the plurality of decomposed signals. The pulsation signal may correspond to the pulsation of the living body, the extra signal may correspond to movement of the living body caused by the vehicle. In this case, even if the time-series data includes information associated with a movement of the living body caused by the vehicle, it is possible to accurately detect the pulsation data.

An example method of obtaining biological data includes generating time-series data in which first to $N^{th}$ distance-based fluctuation data are arranged in time series order, the first to $N^{th}$ distance-based fluctuation data are obtained based on reflected waves which are reflected from a living body at different times arranged in time series order, wherein the reflected waves are wide band radio waves or ultra wide band radio waves, $n^{th}$ distance-based fluctuation data of the first to $N^{th}$ distance-based fluctuation data indicates changes in signal strength with respect to distance. N is a natural number of 2 or more, and n is a natural number of 1 to N. The method also includes generating time-based fluctuation data in which a plurality of corresponding strength information are arranged in time series by performing strength obtaining process on the first to $N^{th}$ distance-based fluctuation data. The strength obtaining process includes obtaining one corresponding strength information of the plurality of corresponding strength information, the one corresponding strength information is a signal strength included in the $n^{th}$ distance-based fluctuation data and based on reflected waves from a predetermined detection part of the living body. The method also includes generating biological data of the detection part of the living body based on the time-based fluctuation data. In this case, the same effect as in the above mentioned biological data obtaining device is obtained.

We claim all modifications and variations coming within the spirit and scope of the subject matter claimed herein.

What is claimed is:

1. A biological data obtaining device, comprising:
a storage unit configured to store time-series data in which first to $N^{th}$ distance-based fluctuation data are arranged in time series order, the first to $N^{th}$ distance-based fluctuation data being obtained based on reflected waves which are reflected from a living body at different times arranged in time series order, wherein the reflected waves are wide band radio waves or ultra wide band radio waves, $n^{th}$ distance-based fluctuation data of the first to $N^{th}$ distance-based fluctuation data indicating a relationship between distance and signal strength, wherein N is a natural number of 2 or more, and wherein n is a natural number of 1 to N;
a first generation unit configured to generate time-based fluctuation data in which a plurality of corresponding strength information are arranged in time series by performing strength obtaining process on the first to $N^{th}$ distance-based fluctuation data, wherein the strength obtaining process includes obtaining one corresponding strength information of the plurality of corresponding strength information, the one corresponding strength information being a signal strength included in the $n^{th}$ distance-based fluctuation data and based on reflected waves from a predetermined detection part of the living body;
a second generation unit configured to generate biological data of the detection part of the living body based on the time-based fluctuation data, the biological data being pulsation data relating to pulsation of the living body; and
a correction unit configured to obtain corrected time-series data by performing correction process on the first to $N^{th}$ distance-based fluctuation data, wherein the correction process includes correcting distance components of the $n^{th}$ distance-based fluctuation data so that a distance component corresponding to the detection part of the living body in the $n^{th}$ distance-based fluctuation data approaches an arbitrary reference value, wherein the first generation unit is configured to obtain signal strengths at the arbitrary reference value from the corrected time-series data as the plurality of corresponding strength information, when performing the strength obtaining process.

2. The device according to claim 1,
wherein the correction process includes correcting distance components of $p^{th}$ to $q^{th}$ distance-based fluctuation data so that an approximate line approaches the arbitrary reference value, the $p^{th}$ to $q^{th}$ distance-based fluctuation data being included in the first to $N^{th}$ distance-based fluctuation data within a predetermined time, the approximate line being obtained based on distance components of signal strength at a peak of the $p^{th}$ to $q^{th}$ distance-based fluctuation data, wherein p and q are natural numbers satisfying $1 \leq p < q \leq N$.

3. The device according to claim 1,
wherein the correction process includes performing block correction process on first to $M^{th}$ blocks that are obtained by sequentially dividing the time-series data in time series order, the block correction process including correcting distance components of a plurality of distance-based fluctuation data of the first to $N^{th}$ distance-based fluctuation data so that an approximate line approaches an arbitrary block reference value, the plurality of distance-based fluctuation data being included in the $m^{th}$ block of the first to $M^{th}$ blocks, the approximate line being obtained based on distance components of signal strength at a peak of the plurality of distance-based fluctuation data, the block reference value being set for each of first to $M^{th}$ blocks, wherein M is a natural number of 2 or more, and wherein m is a natural number of 1 to M.

4. The device according to claim 1,
wherein the first to $N^{th}$ distance-based fluctuation data are obtained based on reflected waves which are reflected from the living body and another living body,
wherein the first generation unit is configured to:
  generate the time-based fluctuation data in which the plurality of corresponding strength information are arranged in time series order by performing the strength obtaining process on the first to $N^{th}$ distance-based fluctuation data, wherein the strength obtaining process includes obtaining the one corresponding strength information of the plurality of corresponding strength information, the one corresponding strength information being a signal strength included in the $n^{th}$ distance-based fluctuation data and based on reflected waves from the predetermined detection part of the living body; and
  generate another time-based fluctuation data in which another plurality of corresponding strength information are arranged in time series order by performing the strength obtaining process on the first to $N^{th}$ distance-based fluctuation data, wherein the strength obtaining process includes obtaining another one corresponding strength information of the another plurality of corresponding strength information, the another one corresponding strength information being a signal strength included in the $n^{th}$ distance-based fluctuation data and based on reflected waves from a predetermined detection part of the another living body,
wherein the second generation unit is configured to:
  generate the pulsation data relating to pulsation of the living body based on the time-based fluctuation data; and
  generate another pulsation data relating to pulsation of the another living body based on the another time-based fluctuation data.

5. The device according to claim 1, further comprising:
a transmitting unit configured to transmit the wide band radio waves or the ultra wide band radio waves; and
a receiving unit configured to receive the reflected waves.

6. A biological data obtaining system, comprising:
the biological data obtaining device according to claim 1;
a transmitting unit configured to transmit the wide band radio waves or the ultra wide band radio waves; and
a receiving unit configured to receive the reflected waves.

7. The system according to claim 6, further comprising:
a communication unit configured to transmit reception data in accordance with the reflected waves to the biological data obtaining device with wireless communication.

8. A biological data obtaining device, comprising:
a storage unit configured to store time-series data in which first to $N^{th}$ distance-based fluctuation data are arranged in time series order, the first to $N^{th}$ distance-based fluctuation data being obtained based on reflected waves which are reflected from a living body at different times arranged in time series order, wherein the reflected waves are wide band radio waves or ultra wide band radio waves, $n^{th}$ distance-based fluctuation data of the first to $N^{th}$ distance-based fluctuation data indicating a relationship between distance and signal strength, wherein N is a natural number of 2 or more, and wherein n is a natural number of 1 to N;
a first generation unit configured to generate time-based fluctuation data in which a plurality of corresponding strength information are arranged in time series by performing strength obtaining process on the first to $N^{th}$ distance-based fluctuation data, wherein the strength obtaining process includes obtaining one corresponding strength information of the plurality of corresponding strength information, the one corresponding strength information being a signal strength included in the $n^{th}$ distance-based fluctuation data and based on reflected waves from a predetermined detection part of the living body; and
a second generation unit configured to generate biological data of the detection part of the living body based on the time-based fluctuation data, the biological data being pulsation data relating to pulsation of the living body,
wherein the second generation unit is configured to:
  generate the pulsation data by performing multiple resolution analysis on the time-based fluctuation data;
  decompose the time-based fluctuation data into a plurality of decomposed signals by performing the multiple resolution analysis on the time-based fluctuation data; and
  generate the pulsation data based on a pulsation signal of the plurality of decomposed signals, the pulsation signal corresponding to the pulsation of the living body.

9. The device according to claim 8,
wherein the second generation unit is configured to generate heartbeat interval data indicating temporal change in heartbeat interval of the living body by spectrally analyzing the pulsation signal using an autoregressive model.

10. The device according to claim 8,
wherein the first to $N^{th}$ distance-based fluctuation data are obtained by oversampling the reflected waves based on a reference frequency corresponding to the pulsation of the living body.

11. The device according to claim 8,
wherein the second generation unit is configured to generate the pulsation data after excluding an extra signal of the plurality of decomposed signals, the extra signal corresponding to movement of the living body different from the pulsation of the living body.

12. A biological data obtaining device, comprising:
a storage unit configured to store time-series data in which first to $N^{th}$ distance-based fluctuation data are arranged in time series order, the first to $N^{th}$ distance-based fluctuation data being obtained based on reflected waves which are reflected from a living body at different times arranged in time series order, wherein the reflected waves are wide band radio waves or ultra wide band radio waves, $n^{th}$ distance-based fluctuation data of the first to $N^{th}$ distance-based fluctuation data indicating a relationship between distance and signal strength, wherein N is a natural number of 2 or more, and wherein n is a natural number of 1 to N;
a first generation unit configured to generate time-based fluctuation data in which a plurality of corresponding strength information are arranged in time series by performing strength obtaining process on the first to $N^{th}$ distance-based fluctuation data, wherein the strength obtaining process includes obtaining one corresponding strength information of the plurality of corresponding strength information, the one corresponding strength information being a signal strength included in the $n^{th}$ distance-based fluctuation data and based on reflected waves from a predetermined detection part of the living body;
a second generation unit configured to generate biological data of the detection part of the living body based on the time-based fluctuation data, the biological data being pulsation data relating to pulsation of the living body; and
a signal strength calculation unit configured to generate the $n^{th}$ distance-based fluctuation data by performing suppressing process on first to $J^{th}$ reception signal data, wherein the first to $J^{th}$ reception signal data are obtained based on reflected waves which are reflected in a detection region in which the living body is present at different times arranged in time series order in a frame period, wherein the reflected waves are the wide band radio waves or the ultra wide band radio waves, wherein $j^{th}$ reception signal data of the first to $J^{th}$ reception signal data indicates changes in signal strength with respect to distance, wherein the $j^{th}$ reception signal data includes signal strengths $a_{j1}$ to $a_{jK}$ in first to $K^{th}$ range bins obtained by dividing the detection region in a distance direction, and wherein J is a natural number of 2 or more, j is a natural number of 1 to J, and K is a natural number of 2 or more, and
wherein the suppressing process includes:
calculating a coefficient $v_i$ based on a result obtained by frequency-converting the signal strengths $a_{1i}$ to $a_{Ji}$ for all of the first to $K^{th}$ range bins, wherein i is a natural number of 1 to K, and
calculating the $n^{th}$ distance-based fluctuation data by multiplying the signal strength $a_{ji}$ by the coefficient $v_i$ in each of the first to $K^{th}$ range bins for the $j^{th}$ reception signal data.

13. The device according to claim 12,
wherein the signal strength calculation unit performs frame set process before performing the suppressing process, and
the frame set process includes obtaining movement information indicating a speed of movement of the living body, and setting a length of the frame period based on the speed indicated by the movement information.

14. A biological data obtaining device, comprising:
a storage unit configured to store time-series data in which first to $N^{th}$ distance-based fluctuation data are arranged in time series order, the first to $N^{th}$ distance-based fluctuation data being obtained based on reflected waves which are reflected from a living body at different times arranged in time series order, wherein the reflected waves are wide band radio waves or ultra wide band radio waves, $n^{th}$ distance-based fluctuation data of the first to $N^{th}$ distance-based fluctuation data indicating a relationship between distance and signal strength, wherein N is a natural number of 2 or more, and wherein n is a natural number of 1 to N;
a first generation unit configured to generate time-based fluctuation data in which a plurality of corresponding strength information are arranged in time series by performing strength obtaining process on the first to $N^{th}$ distance-based fluctuation data, wherein the strength obtaining process includes obtaining one corresponding strength information of the plurality of corresponding strength information, the one corresponding strength information being a signal strength included in the $n^{th}$ distance-based fluctuation data and based on reflected waves from a predetermined detection part of the living body;
a second generation unit configured to generate biological data of the detection part of the living body based on the time-based fluctuation data, the biological data being pulsation data relating to pulsation of the living body; and
a signal strength calculation unit configured to generate the $n^{th}$ distance-based fluctuation data by performing suppressing process on first to $J^{th}$ reception signal data, wherein the first to $J^{th}$ reception signal data are obtained based on reflected waves which are reflected in a detection region in which the living body is present at different times arranged in time series order in a frame period, wherein the reflected waves are the wide band radio waves or the ultra wide band radio waves, wherein $j^{th}$ reception signal data of the first to $J^{th}$ reception signal data indicates changes in signal strength with respect to distance, wherein the $j^{th}$ reception signal data includes signal strengths $a_{j1}$ to $a_{jK}$ in first to $K^{th}$ range bins obtained by dividing the detection region in a distance direction, and wherein J is a natural number of 2 or more, j is a natural number of 1 to J, and K is a natural number of 2 or more, and
wherein the suppressing process includes:
calculating a coefficient $v_i$ based on a result obtained by frequency-converting the signal strengths $a_{1i}$ to $a_{Ji}$ for all of the first to $K^{th}$ range bins, wherein i is a natural number of 1 to K;
generating integrated signal data by integrating a plurality of reception signal data of the first to $J^{th}$ reception signal data, wherein the integrated signal data include signal strengths $b_1$ to $b_K$ in the first to $K^{th}$ range bins; and calculating the $n^{th}$ distance-based fluctuation data by multiplying the signal strength $b_i$ by the coefficient $v_i$ in each of the first to $K^{th}$ range bins for the integrated signal data.

15. A vehicle, comprising:
a biological data obtaining device comprising:
- a storage unit configured to store time-series data in which first to $N^{th}$ distance-based fluctuation data are arranged in time series order, the first to $N^{th}$ distance-based fluctuation data being obtained based on reflected waves which are reflected from a living body at different times arranged in time series order, wherein the reflected waves are wide band radio waves or ultra wide band radio waves, $n^{th}$ distance-based fluctuation data of the first to $N^{th}$ distance-based fluctuation data indicating a relationship between distance and signal strength, wherein N is a natural number of 2 or more, and wherein n is a natural number of 1 to N;
- a first generation unit configured to generate time-based fluctuation data in which a plurality of corresponding strength information are arranged in time series by performing strength obtaining process on the first to $N^{th}$ distance-based fluctuation data, wherein the strength obtaining process includes obtaining one corresponding strength information of the plurality of corresponding strength information, the one corresponding strength information being a signal strength included in the $n^{th}$ distance-based fluctuation data and based on reflected waves from a predetermined detection part of the living body; and
- a second generation unit configured to generate biological data of the detection part of the living body based on the time-based fluctuation data, the biological data being pulsation data relating to pulsation of the living body, wherein the second generation unit is configured to:
- decompose the time-based fluctuation data into a plurality of decomposed signals by performing multiple resolution analysis on the time-based fluctuation data; and
- generate the pulsation data based on a pulsation signal of the plurality of decomposed signals after excluding an extra signal of the plurality of decomposed signals, the pulsation signal corresponding to the pulsation of the living body, the extra signal corresponding to movement of the living body caused by the vehicle.

* * * * *